(12) United States Patent
Liang et al.

(10) Patent No.: US 8,685,923 B2
(45) Date of Patent: *Apr. 1, 2014

(54) FIBRILLAR ALBUMIN FOR USE IN INHIBITING CANCER GROWTH

(75) Inventors: Shu-Mei Liang, Bethesda, MD (US); Chun-Yung Huang, Tainan County (TW); Chi-Ming Liang, Taipei (TW)

(73) Assignee: Academia Sinica, Taipei (TW)

( * ) Notice: Subject to any disclaimer, the term of this patent is extended or adjusted under 35 U.S.C. 154(b) by 100 days.

This patent is subject to a terminal disclaimer.

(21) Appl. No.: 13/572,652

(22) Filed: Aug. 12, 2012

(65) Prior Publication Data

US 2012/0316117 A1 Dec. 13, 2012

Related U.S. Application Data

(60) Division of application No. 12/082,634, filed on Apr. 11, 2008, now Pat. No. 8,268,974, which is a continuation-in-part of application No. 11/949,125, filed on Dec. 3, 2007, now Pat. No. 7,700,730, and a continuation-in-part of application No. 11/748,294, filed on May 14, 2007, now Pat. No. 7,604,961, said application No. 11/949,125 is a division of application No. 10/863,637, filed on Jun. 8, 2004, now Pat. No. 7,323,546, which is a continuation-in-part of application No. 10/449,531, filed on May 29, 2003, now Pat. No. 7,217,784, said application No. 11/748,294 is a division of application No. 10/449,531.

(60) Provisional application No. 61/036,432, filed on Mar. 13, 2008.

(51) Int. Cl.
*A61K 38/38* (2006.01)
*C07K 14/76* (2006.01)
*C07K 1/16* (2006.01)

(52) U.S. Cl.
USPC .................. 514/15.2; 530/362; 530/417

(58) Field of Classification Search
None
See application file for complete search history.

(56) References Cited

PUBLICATIONS

Adachi et al., Clin. Cancer Res., 2000, 6:96-101.*
Mierke et al., Journal of Cell Science, 2010, 124(3):369-383.*
Sawada et al., Journal of Oncology, 2012, vol. 2012, Article ID 915140: 1-6.*
Stachurska et al., Cell Biol. Int., 2012, 36:883-892.*

* cited by examiner

*Primary Examiner* — Nicole Kinsey White
(74) *Attorney, Agent, or Firm* — Hsiu-Ming Saunders; Intellectual Property Connections, Inc.

(57) ABSTRACT

A method for inhibiting survival of cancer cells in a subject is disclosed. The method comprises administering to a subject in need thereof a therapeutically effective amount of fibrillar albumin. The preparation of the fibrillar albumin comprises: (i) forming a solution comprising an isolated and/or purified globular albumin; (ii) adding a detergent to the solution containing the isolated and/or purified globular albumin, wherein the detergent is one selected from the group consisting of sodium dodecyl sulfate (SDS) and n-tetradecyl-N,N-dimethyl-3-ammonio-1-propanesulfonate; (iii) applying the solution to a molecular sizing column with a pore size that permits separation of a protein with a molecular weight of at least about 70 kDa so as to promote column-induced formation of the fibrillar albumin from the isolated and/or purified globular albumin; and (iv) eluting the fibrillar albumin from the column, wherein the eluted albumin has a fibrillar structure.

18 Claims, 13 Drawing Sheets

FIG. 11

SEQUENCE LISTING

<160> NUMBER OF SEQ ID NOS: 2

<210> SEQ ID NO 1
<211> LENGTH: 33
<212> TYPE: DNA

-continued

```
<213> ORGANISM: Artificial Sequence
<220> FEATURE:
<223> OTHER INFORMATION: Primer for amplifying VP3 gene

<400> SEQUENCE: 1
ccgggatcca agcttgggat tttccccgtg gca                                33

<210> SEQ ID NO 2
<211> LENGTH: 27
<212> TYPE: DNA
<213> ORGANISM: Artificial Sequence
<220> FEATURE:
<223> OTHER INFORMATION: Primer for amplifying VP3 gene

<400> SEQUENCE: 2
ccgctcgagt tgggttcggg cgtcgac                                       27
```

FIBRILLAR ALBUMIN FOR USE IN INHIBITING CANCER GROWTH

RELATED APPLICATIONS

This application is a division of and claims priority to U.S. application Ser. No. 12/082,634, filed Apr. 11, 2008, now issued as U.S. Pat. No. 8,268,974, which is a continuation-in-part of, and claims priority to Ser. No. 11/949,125, filed Dec. 3, 2007 and now issued as U.S. Pat. No. 7,700,730, and Ser. No. 11/748,294, filed May 14, 2007 and now issued as U.S. Pat. No. 7,604,961. Ser. No. 11/949,125 is a division of and claims priority to U.S. application Ser. No. 10/863,637, filed Jun. 8, 2004 and now issued as U.S. Pat. No. 7,323,546. Ser. No. 10/863,637 is a continuation-in-part of, and Ser. No. 11/748,294 is a division of, and both claim priority to, U.S. application Ser. No. 10/449,531, filed May 29, 2003, now issued as U.S. Pat. No. 7,217,784. Ser. No. 12/082,634 claims priority to U.S. Provisional Application. No. 61/036,432, filed on Mar. 13, 2008. The contents of each and all referenced patent applications are incorporated herein by reference.

FIELD OF THE DISCLOSURE

The present disclosure presents a method of folding a fibrillar structure from an unfolded native protein and utilizing the fibrillar structure protein to induce cell apoptosis and as vaccine adjuvants.

BACKGROUND

Studies have found that some proteins form fibrillar structures after glycation (Bouma, et al. *J Bio Chem* 278(43): 41810-41819: 2003), incubation at high temperature (Sagis, et al. *Langmuir* 20(3):924-927: 2004), or sonication (Stathopulos, et al. *Protein Sci* 13(11):3017-3027: 2004). However, these methods often require a high concentration of protein, vigorous shaking, assistance of fibril seed, and generally take a long time, even up to a month of incubation at ambient temperature. In addition, unless aggregates form and precipitate out, such methods cannot isolate fibrillar from non-fibrillar proteins.

SUMMARY

A method is disclosed for changing a globular protein structure into a fibrillar protein structure. The method comprises the steps of providing a globular protein, forming a solution containing the globular protein, adding a detergent to the solution containing the globular protein, and applying the solution to a molecular sizing column with a pore size of at least about 70 kDa. In one aspect the method includes eluting the fibrillar protein with a solution containing detergent.

In another aspect of the present disclosure, a method is disclosed for treating cancer. The method comprises the steps of providing a protein, changing the protein into a fibrillar structure, and administering a therapeutically effective amount of the fibrillar structure protein to a patient in need thereof.

A method for producing an adjuvant is disclosed. The method comprises the steps of providing a protein, and changing the protein into a fibrillar structure.

DRAWINGS

The above-mentioned features and objects of the present disclosure will become more apparent with reference to the following description taken in conjunction with the accompanying drawings wherein like reference numerals denote like elements and in which:

FIGS. 1*a-e* are TEM images of various proteins.

FIG. 1*f* is a graph illustrating the fluorescence levels of thioflavin T (ThT) in relation to different concentrations of BSA-S200.

FIG. 2*a* is a TEM image of BSA-Zwit.

FIG. 2*b* is a TEM image of BSA-HW55S.

FIG. 3*a* is a bar graph illustrating cell cytotoxicity in relation to different concentrations of various proteins.

FIG. 3*b* is a Western blot illustrating the effect of BSA-S200 on Akt varying concentrations of anti-α5β1 antibodies.

FIG. 3*c* is a bar graph illustrating cell cytotoxicity in relation to different concentrations of BSA-S200 and anti-α5β1 antibodies.

FIG. 4 is a collection of bar graphs illustrating cell cytotoxicity in relation to the RGD motif and molecular weight of various proteins.

FIG. 5*a-b* are microscope images of BHK-21 cells incubated with various proteins.

FIG. 5*c* is a graph illustrating caspase-3 activity.

FIG. 6*a* is a graph illustrating cell cytotoxicity in relation to various concentrations of BSA-S200.

FIG. 6*b* is an immunoblot illustrating the binding of integrin α5β1 protein with BSA-S200 and native BSA.

FIG. 7*a-d* are Western blots of BHK-21 cells treated with F-BSA and anti-integrin α5β1 antibody.

Figure 1:
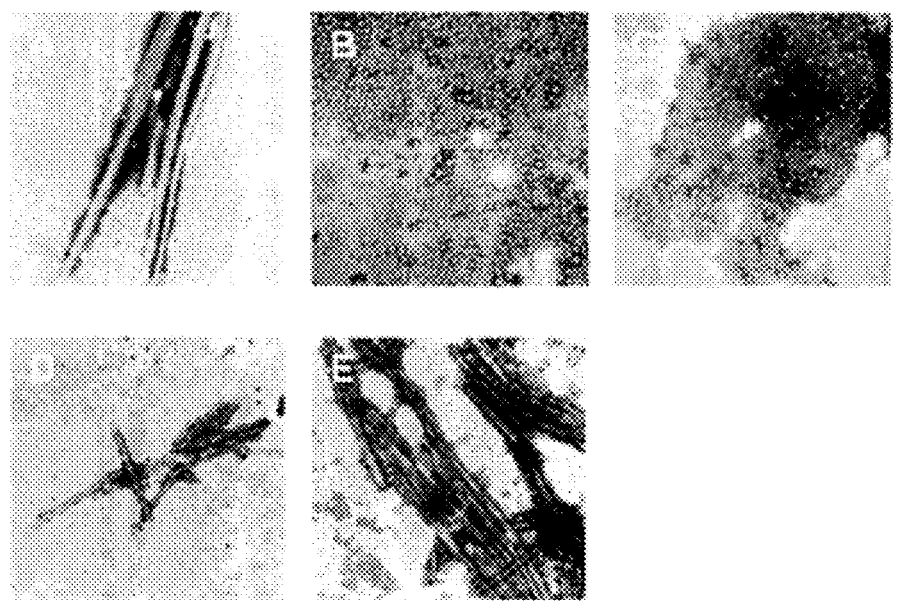
Figure 1:
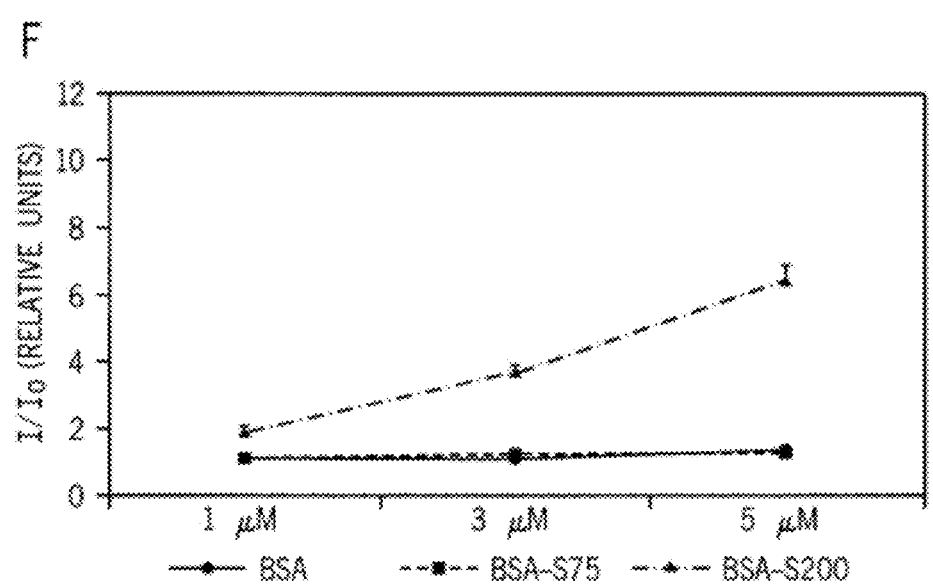

FIG. 10*a-e* are TEM images showing the structure of various proteins.

FIG. 10*f-g* are graphs illustrating the fluorescence levels of ThT in relation to different concentrations of BSA-S200 and FN-S200.

FIG. 11*a* are immunoblots illustrating the binding of anti-TLR2 antibody and anti-FMDV antibody to lysate from RAW 264.7 cells.

FIG. 11*b-g* are immunofluorescence staining images of BSA and BSA-S200.

FIG. 12*a-d* are graphs illustrating NFκB reporter luciferase levels of cells treated with various proteins.

FIG. 13*a-c* are graphs illustrating IL-6 and IL-8 expression of RAW 264.7 cells incubated with different concentrations of various proteins.

DETAILED DESCRIPTION

The present disclosure relates to a process of producing fibrillar proteins and methods of treatment using fibrillar proteins. This process has advantages which include ease of control, homogeneity of production, and feasibility of scaling up. Moreover, fibrillization of proteins can be induced by this process without the assistance of fibril seed. Even a tiny amount of protein would be applicable to this process. As used herein, "protein" includes one or more proteins, protein fragments, polypeptides or peptides. Proteins include both synthetic and naturally occurring proteins.

According to the present disclosure, a method is disclosed for changing a globular protein structure into a fibrillar protein structure. The method can be used to convert native proteins, regardless of their sequence, into fibrillar form in a simple and rapid manner. The method comprises the steps of providing a globular protein and applying the protein to a molecular sizing column with a pore size of at least 70 kDa, and eluting the protein with a solution containing detergent.

In an exemplary implementation, the method comprises the steps of providing a globular protein, forming a solution containing the globular protein, adding a detergent to the solution containing the globular protein, and applying the solution to a molecular sizing column with a pore size of at least 70 kDa.

In an exemplary implementation, the method comprises the steps of providing a globular protein, forming a solution containing the globular protein, adding a detergent to the solution containing the globular protein, and applying the solution to a molecular sizing column with a pare size of at least about 70 kDa in the presence of low concentration of detergent.

In another aspect of the present disclosure, a method is disclosed for changing an unfolded protein structure into a fibrillar protein structure. The method comprises the steps of providing an unfolded protein and applying the protein to a molecular sizing column with the presence of urea. In an exemplary implementation, the method comprises the steps of providing an unfolded protein in the presence of 8 M urea and applying the protein to a molecular sizing column with a pore size of less than 70 kDa in the presence of detergent. The added urea to unfold the protein need not be limited to 8M. Other molar ratios will result in unfolding, the degree of unfolding is related to the protein being unfolded.

Globular proteins, also known as spheroproteins, are one of two main tertiary structure classes of proteins. Globular proteins are generally soluble and form spheriodal molecules in water. They have a complex secondary structure comprising a mixture of secondary structure motifs, such as α-helices, β-sheets, and loop structures. The other main tertiary structure class of proteins are fibrillar proteins, or fibrous proteins. Fibrillar proteins are generally insoluble and have an elongated shape. They have a simpler secondary structure and are often based on only one type of secondary structure motif.

In exemplary implementations, the globular protein is an albumin, fibronectin, recombinant caspid protein VP1 of the foot-and-mouth-disease virus (rVP1), recombinant caspid protein VP2 of the foot-and-mouth-disease virus (rVP2), recombinant caspid protein VP3 of the foot-and-mouth-disease virus (rVP3), or precursor protein P1 of VP1, VP2, VP3, and VP4. The protein may also be a chimeric protein comprising parts from VP1, VP2, VP3, and/or VP4, for example VP42, which comprises parts of both VP2 and VP4. Other globular proteins may also be used, including both naturally-occurring proteins and synthetic oligopeptides. The globular protein is generally dissolved into solution form. In an exemplary implementation, the globular protein is dissolved in PBS.

Surfactants, also referred to herein as detergents, are substances that lower the surface tension of water and increase the solubility of organic compounds. Detergents may be ionic, which includes cationic, anionic, and zwitterionic detergents, as well as non-ionic. Detergents play a role in disrupting non-covalent bonds in proteins, thereby denaturing the proteins such that they lose their native shape or conformation. In exemplary implementations, the detergent used is sodium dodecyl sulfate (SDS), obtained from Sigma. In other exemplary implementations, the detergent used is Zwittergent 3-14, obtained from Calbiochem.

Amyloids are fibrous cross-β protein aggregates. Numerous proteins are capable of converting to amyloid-like fibrils with characteristics that include fibrillar morphology, protofilament substructure, cross-β diffraction pattern, an increase in β-structure, Congo red binding, and ThT binding.

In exemplary implementations, the globular protein is converted to form amyloid-like fibrils, which allows for the converted protein to be identified by its amyloid-like properties.

Chromatography may be used in the process to convert the globular protein structure into a fibrillar protein structure and separate them. Generally, chromatography is accomplished using columns, though other methods such as those used for thin-layer chromatography may also be possible. Chromatography techniques include size exclusion, affinity, and ion-exchange. Though a batch-type production of fibrillar proteins is possible, utilizing a column process allows globular proteins to be converted into a fibrillar form in a rapid, steady, efficient, and continuous manner. Scaling-up this process is also possible with the usage of columns.

In exemplary implementations, size exclusion chromatography with bead pore sizes of at least about 70 kDa is used. The bead pore size used may vary depending on various characteristics of the globular protein, for example its size. The pore size plays a role in allowing proteins to enter the bead matrix, thus leading to mechanical forces which contribute to protein unfolding/folding and enhance fibrillogenic ensemble. In exemplary implementations, the molecular sizing column used is a Superdex 200. In other exemplary implementations, the molecular sizing column used is a HW55S.

For column chromatography, a buffer solution containing low concentration(s) of detergent may be used to elute the column. In some aspects the molecular sizing column is eluted with a buffer solution containing 25 mM Tris-HCL, pH 8.0, 1 mM EDTA, 0.1 M NaCl, and 0.05% SDS. In other exemplary implementations, the molecular sizing column is eluted with a buffer solution containing 25 mM Tris-HCL, pH 8.0, 1 mM EDTA, 0.1 M NaCl, and 0.05% Zwittergent 3-14. The eluant may be collected as fractions and the fractions containing the fibrillar protein subsequently pooled together. The pooled fraction may then be further filtered to purify and isolate the fibrillar protein, for example dialyzing against PBS to remove SDS.

In another aspect of the present disclosure, a method is disclosed for treating cancer. The method comprises the steps of providing a protein, changing the protein into a fibrillar structure, and administering a therapeutically effective amount of the fibrillar structure protein to a patient in need thereof. Conversion of proteins into fibrillar form increases their cytotoxic effects on target cells.

In exemplary implementations, the cancer is a kidney, breast, lung, prostate, liver, or ovarian cancer. The protein used to treat the cancer is an albumin, fibronectin, rVP1, rVP2, rVP3, P1, or chimeric protein comprising parts from VP1, VP2, VP3, and/or VP4. In exemplary implementations, the fibrillar protein plays a role in inducing cancer cell apoptosis by modulating the Akt signaling pathway. In some instances, the fibrillar protein modulates integrin α5β1 or αvβ3 which leads to the deactivation of Akt. In other instances, fibrillar albumin binds to integrin and causes cellular apoptosis mainly through the integrin/FAK/Akt/GSK-3β/caspase-3 pathway.

According to exemplary implementations, the protein may be administered as part of a composition. The composition may be in various forms including powders, creams, gels, salves, ointments, solutions, tablets, capsules, sprays, and patches. Vehicles and carriers may be used for delivery of the composition to the patient. Such carriers include solubilizing agents, diluents, and dispersion media. These carriers are biocompatible, pharmaceutically acceptable, and do not alter the treatment characteristics of the fibrillar protein. Excipients, adjuvants and other ingredients may also be included in the composition.

Administration of the composition may be achieved through various methods to different parts of the body, including intravenous, intradermal, subcutaneous, oral (e.g., inhalation), transdermal (i.e., topical), transmucosal, intraperitoneal, intratumoral, and rectal administration.

The phrase "therapeutically effective amount" refers to an amount that produces some desired effect at a reasonable benefit/risk ratio applicable to any medical treatment. The effective amount may vary depending on such factors as the disease or condition being treated, the particular targeted constructs being administered, the size of the subject, or the severity of the disease or condition. One of ordinary skill in the art may empirically determine the effective amount of a particular compound without necessitating undue experimentation.

The protein for treating the cancer may be selected based on the severity of the disease and the desired cytotoxicity to the cancer cells. In exemplary implementations, for greater cytotoxicity to the cancer cells, a protein with an RGD motif and/or greater molecular weight is selected.

In another aspect of the present disclosure, a method for producing a vaccine is disclosed. The method comprises the steps of providing a protein, and changing the protein into a fibrillar structure. This fibrillar structure protein may then be administered to a patient as a vaccine against a specific disease.

In another aspect of the present disclosure, a method for producing a vaccine or immunologic adjuvant is disclosed. The method comprises the steps of providing a protein, and changing the protein into a fibrillar structure. An adjuvant may not have any specific antigenic effects in itself, but may stimulate the immune system, increasing the response to a vaccine. In exemplary implementations, the protein activates innate immune responses through toll-like receptor 2 (TLR2). The fibrillar protein activates TLR2 to induce cytokine production while the protein in its native state does not.

In other implementations, an antigen may be converted into fibrillar form to have both antigenic and adjuvant effects, making the antigen a vaccine without the need for additional adjuvants to boost immune responses.

EXAMPLES

A more complete understanding of the present disclosure can be obtained by reference to the following specific examples and figures. The examples and figures are described solely for purposes of illustration and are not intended to limit the scope of the disclosure. Changes in form and substitution of equivalents are contemplated as circumstances may suggest or render expedient. Although specific terms have been employed herein, such terms are intended in a descriptive sense and not for purposes of limitations. Modifications and variations of the disclosure as hereinbefore set forth can be made without departing from the spirit and scope thereof, and therefore, only such limitations should be imposed as are indicated by the appended claims.

Example 1

Materials and Methods

Materials. The antibodies against phospho-Ser$^{473}$ Akt was obtained from Cell Signaling Technology, Inc. Zwittergent 3-14 was obtained from Calbiochem. Fibronectin (FN), Anti-actin antibody, anti-integrin α5β1 polyclonal antibody (function-blocking antibody), horseradish peroxidase-coupled anti-mouse IgG secondary antibodies, horseradish peroxidase-coupled anti-rabbit IgG secondary antibodies and MTT assay kit were purchased from Chemicon International, Inc. BSA was purchased from Bio Basic Inc. Thioflavin T (ThT) and sodium dodecyl sulfate (SDS) were purchased from Sigma.

Expression and purification of recombinant VP1 and VP3. VP1 and VP3 are the components of capsid proteins of foot-and-mouth disease virus (FMDV). The recombinant VP1 proteins, after expressed in E. coli., were purified and refolded according to a procedure described previously (Yang, et al. *Journal of Gene Medicine* 7:708-717: 2005). The VP3 gene was amplified by PCR from the plasmid pIBSY1-P1 with 5'-CCGGGATCCAAGCTTGGGATTTTCCCCGTGGCA-3' (SEQ ID NO: 1) and 5'-CCGCTCGAGTT GGGT-TCGGGCGTCGAC-3' (SEQ ID NO: 2) as primers, which introduced a BamHI site at the N-terminus and a XhoI site at the C-terminus, respectively. After restriction enzyme digestion, the amplified gene was ligated between the BamHI and the XhoI site of pET24a (+) (Novagene, Wis.) and transformed into DH5$\alpha$ competent cells. The identified positive clone, verified by sequencing, was used to transform *E. coli* BL21 (DE3) competent cells. The recombinant VP3 protein, after expressed in *E. coli*., was also purified and refolded according to the procedure described previously (Yang, et al. *Journal of Gene Medicine* 7:708-717: 2005).

Preparation of BSA fibrillar proteins. Twenty mg BSA (from Bio Basic Inc.) was dissolved in 10 ml PBS and SDS (10%; w/v) was then added until it reached the final concentration of 1%. After sonication for 5 min in water sonicator, the SDS-containing protein solution was subsequently applied to a Superdex-200 column (2.6 cm×100 cm, Amersham Biosciences), which was previously equilibrated with a buffer solution containing 25 mM Tris-HCl, pH 8.0, 1 mM EDTA, 0.1 M NaCl, and 0.05% SDS. Fractions containing BSA were pooled. The pooled fractions were then dialyzed against PBS to remove SDS. Fibronection fibrillar protein was also prepared by using the same protocol.

Transmission electron microscope (TEM). For transmission electron microscope (TEM) analyses of fibrillar proteins, 1 mg/ml of proteins were applied to 200-mesh carbon-coated copper grids. Excess samples were removed and the grids were air-dried. The protein-bearing grids were negatively stained with 1% (W/V) phosphotungstic acid for 1 min. Transmission electron micrographs were observed at 20,000-150,000× magnification at 75 kV on a Hitachi H-7000 electron microscope.

Thioflavin T (ThT) fluorescence. Thioflavin T (ThT) is one of the markers for amyloid-like properties. For fluorescence measurements, increasing concentrations of proteins (1 μM, 3 μM and 5 μM) were incubated with 20 μM ThT. After 1 h of incubation at room temperature, fluorescence was measured in triplicate on a Wallac VICTOR$^2$ 1420 Multilabel Counter (Perkin Elmer life science). Excitation and emission wavelengths were 355 nm and 535 nm, respectively. ThT background signal from buffer was subtracted from corresponding measurements.

Cell lines and treatment. BHK-21 cells (from hamster kidney) and T47D cell lines (human breast duct carcinoma) were maintained at 37° C. in Dulbecco's modified Eagle's medium (DMEM) supplemented with 10% fetal bovine serum (FBS), 2 mM L-glutamine, 100 units/ml penicillin, and 100 μg/ml streptomycin. Cells were cultured in monolayer cultures overnight. The cells were washed twice with PBS and treated with proteins in DMEM without FBS for indicated time. Some of the cells were then lysed with 0.2 ml of lysis buffer (Pierce) at the indicated time points, and 20-μl samples were analyzed for Akt phosphorylation by Western blotting.

Cell survival assay. Cell survival was determined by MTT colorimetric assay. Exponentially growing cells ($1\times10^4$ for BHK-21 cells; $1.25\times10^4$ for T47D cell lines) were plated in 96-well plates in DMEM with 10% FBS and, after 24 h of growth, treated with a series of concentrations of fibrillar proteins in DMEM without FBS for 8 h at 37° C. After treatment, the MTT solution was added to each well (0.5 mg/ml) and incubated for 4 h. The viable cell number is directly proportional to the production of formazan which, following solubilization with isopropanol, can be measured spectrophotometrically at 560 nm in an ELISA plate reader.

SDS-PAGE and Immunoblot analyses. Samples were separated on 10% SDS-PAGE gels in Hoefer vertical gel apparatuses (Amersham Biosciences), followed by electrophoretic transfer to polyvinylidene difluoride membranes (Pall Corporation). The membranes were blocked with 5% skimmed milk powder in PBST for 1 h, and incubated with primary antibody (5-10 µg/ml) in blocking buffer. The membranes were then washed in PBST, followed by incubation with horseradish peroxidase-conjugated secondary antibody (Chemicon). The antibodies were detected with chemiluminescence (SuperSignal West Pico, Pierce) by exposure to Biomax ML film (Eastman Kodak).

Figures

FIG. 1. Superdex-200 chromatography but not Superdex-75 chromatography promotes the formation of fibrillar proteins. TEM images show fibrillar structure of BSA-S200 (A) but globular structure of BSA-S75 (B). BSA, as a control, also displays globular structure (C), (D) and (E), VP1-S200 and VP3-S200, two recombinant proteins expressed in E. coli. and refolded in Superdex200 column, exhibit fibrillar structure by TEM assay. F, incubation of increasing concentrations of BSA-S200 with 20 µM amyloid-specific dye ThT results in increased levels of fluorescence of ThT, as compared to BSA and BSA-S75. The values are from three measurements. Data represent means±S.D. (n=3).

Figure 2:
Figure 2:

FIG. 2. The formation of amyloid-like fibrils is irrespective to detergent or bead matrix. TEM images show fibrillar structures of BSA-Zwit (A) and BSA-HW55S (B).

Figure 3:
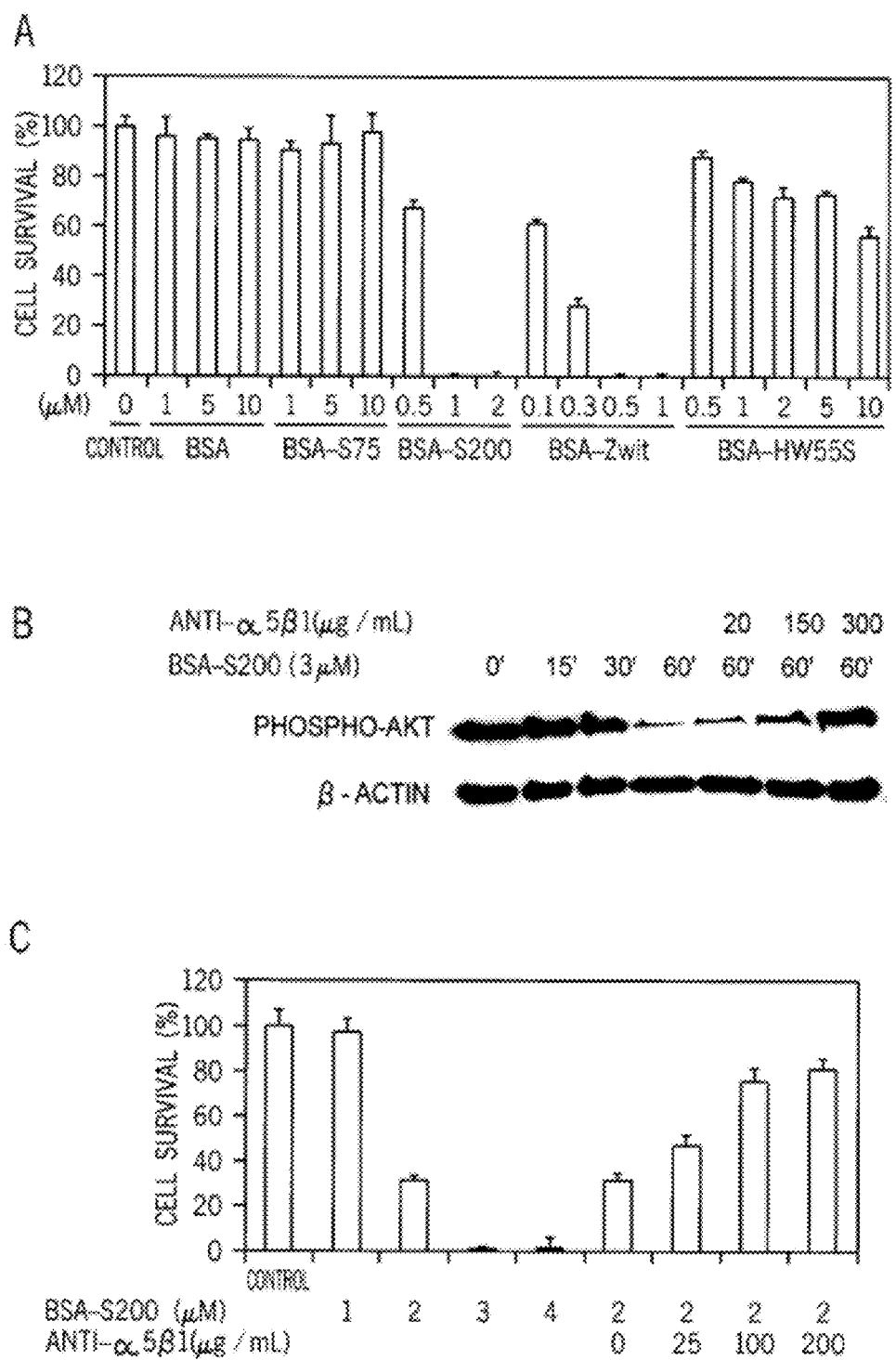

FIG. 3. Fibrillar proteins-induced cell death is via the Akt signal pathway. BHK-21 cells were treated with various concentrations of BSA, BSA-S75, BSA-S200, BSA-Zwit, or BSA-HW55S for 8 h in serum-free medium. After treatment, cell survival was determined by the MTT assay. Data represent means±S.D. (n=3) (A). BHK-21 cells were pre-treated with or without anti-α5β1 antibodies for 30 min, then treated with 3 µM BSA-S200 for indicated time. After treatment, cell lysates were analyzed by Western blotting using anti-phospho-Akt (p-Akt) as the primary antibodies (B). C, T47D cell lines were pre-treated with or without anti-α5β1 antibodies for 30 min, then treated with varying concentrations of BSA-S200 for 8 h in serum-free medium. After treatment, cell viability was determined by the MIT assay. Data represent means±S.D. (n=3).

Figure 4:
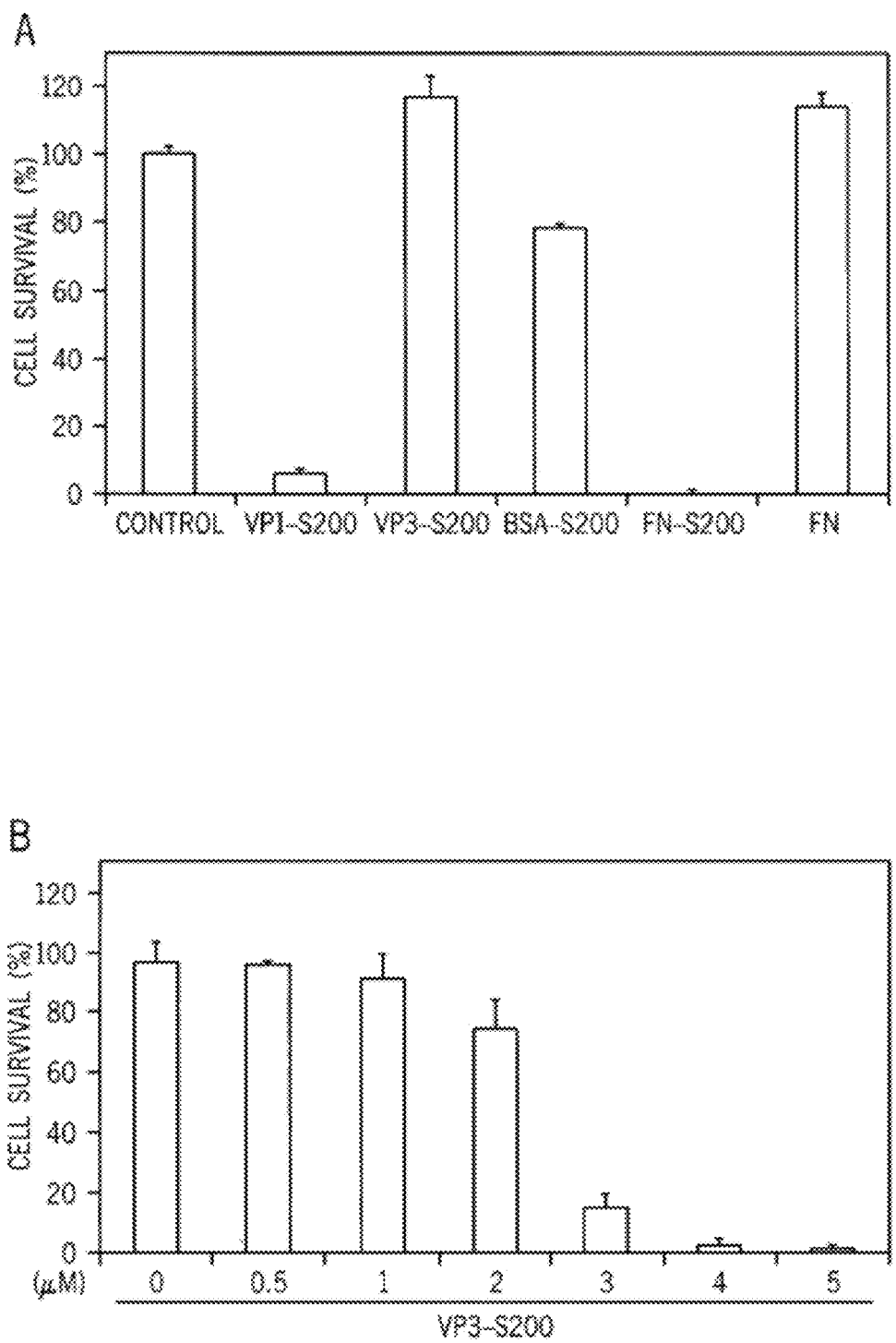

FIG. 4. The effect of rgd motif and molecular weight of fibrillar protein on the cytotoxicity of BHK-21 cells. (A), BHK-21 cells were treated with 0.5 µM VP1-S200, VP3-S200, BSA-S200, FN-S200, or FN for 8 h in serum-free medium. After treatment, cell survival was determined by the MIT assay. Data represent means±S.D. (n=3). (B), BHK-21 cells were treated with increasing concentrations of VP3-S200 for 8 h in serum-free medium. After treatment, cell survival was determined by the MTT assay. Data represent means±S.D. (n=3).

Results

Effect of column bead pore size and bead matrix on the formation of amyloid-like fibrils. Bovine serum albumin (BSA) is a globular protein. SDS was added to the BSA solution and they were applied to a Superdex-200 column (with pore size up to 600 KDa) and then eluted with a buffer solution containing 25 mM Iris-HCl, pH 8.0, 1 mM EDTA, 0.1 M NaCl, and 0.05% SDS. The BSA protein obtained from Superdex-200 column (BSA-S200) exhibited fibrillar structure as shown by Transmission electron microscope (TEM) analyses (FIG. 1A) and enhanced fluorescence of amyloid specific dye Thioflavin T (ThT) in a dose-dependent manner (FIG. 1F). To investigate the effect of column bead pore size on the formation of fibrils, a Superdex-75 column was used with a smaller pore size of only 3-70 kDa MW range for this study (Table 1). TEM analyses revealed that BSA eluted from Superdex 75 (BSA-S75), like BSA, showed globular structure (FIGS. 1, B and C) and did not enhance fluorescence of amyloid specific dye ThT (FIG. 1F). Recombinant VP1 (rVP1) and recombinant VP3 (rVP3) expressed in E. Coli., extracted by urea and purified by affinity column, were also subjected to chromatography, with detergent, and refold through a Superdex-S200 column as described. TEM data showed VP1-S200 (FIG. 1D) and VP3-S200 (FIG. 1E) also exhibited fibrillar structure. The effect of column bead matrix on fibrillar protein formation then examined. HW55S beads that have similar bead properties (with pore size up to 700 KDa) as Superdex-200 but different matrix composite (Table 1) were used for comparison. BSA eluted from HW55S chromatography (BSA-HW55S) displayed fibrillar structure as monitored by TEM (FIG. 2B). These data suggest that molecular sizing column such as Superdex-200 (S200) and HW55S that have pore size more than 70 kDa promotes the formation of amyloid-like fibrillar proteins.

TABLE 1

Comparison of properties of Superdex-200, Superdex-75, and HW55S chromatography.

| Properties | Column chromatography | | |
| --- | --- | --- | --- |
| | Superdex 200 | Superdex 75 | HW55S |
| Company | Amersham Biosciences | Amersham Biosciences | TOSOH Corporation |
| Matrix | cross-linked agarose and dextran | cross-linked agarose and dextran | Hydroxylated methacrylic polymer |
| Particle size | 24-44 µm | 24-44 µm | 20-40 µm |
| Pore size | 10-600 kDa MW range (proteins) | 3-70 kDa MW range (proteins) | 1-700 kDa MW range (proteins) |

Effect of detergent on the formation of amyloid-like fibrils. Zwittergent 3-14, a detergent that retained its zwitterionic character over a wide pH range, presumably does not irreversibly bind to either anionic or cationic compounds. Here the effect of Zwittergent 3-14 on the formation of fibrillar BSA from Superdex-200 chromatography was investigated. Zwittergent 3-14 was added to the BSA solution (1% Zwittergent 3-14) and refolded by and/or on passage through a Superdex-200 column eluted with a buffer solution containing 25 mM Tris-HCl, pH 8.0, 1 mM EDTA, 0.1 M NaCl, and 0.05% Zwittergent 3-14. The BSA protein obtained from Superdex-200 column with Zwittergent 3-14 (BSA-Zwit) exhibited fibrillar structure under TEM (FIG. 2A). These data suggest that detergent such as SDS and Zwittergent 3-14 and bead pore size are important for fibrillar protein formation.

Fibrillar proteins induced cell death via deactivating Akt. It has been shown previously that rVP1 is cytotoxic to BHK-21 cell as well as various cancer cell lines. To examine whether fibrillar proteins induced by our method are cytotoxic to cells, BHK-21 cells were treated with various concentrations of BSA-S200, BSA-Zwit, or BSA-HW55S in serum-free medium. It was found that BSA-S200, BSA-Zwit, and BSA-HW55S all caused cell death in a dose-dependent manner (FIG. 3A). BSA-Zwit exhibited the strongest cytotoxicity among all tested. At 0.5 µM concentration, it induced near 100% cytotoxicity whereas BSA-S 200 induced 35% and BSA-HW55S induced 10% cytotoxicity. The $IC_{50}$ for BSA-Zwit, BSA-S200 and BSA-HW55S was 0.2, 0.75 and more than 10 µM, respectively. As controls, two globular proteins, native BSA and BSA-S75 were used and found to induce little, if any, cytotoxicity to cells (FIG. 3A). To demonstrate if fibrillar proteins-induced cell death is via Akt signaling pathway, BHK-21 cells were pre-treated with or without anti-α5β1 antibodies for 30 min, then treated with 3 µM BSA-S200 for indicated time. Data revealed that BSA-S200, like rVP1-S200 and rVP3-S200, deactivated Akt in a time-dependent manner. Besides, the inhibitory effect of BSA-S200 on Akt was reversed by pretreatment of increasing concentrations of anti-α5β1 antibodies (FIG. 3B).

Moreover, the effect of anti-α5β1 antibodies on cell death induced by fibrillar proteins was examined. Pretreatment of T47D cell lines (a breast cancer line) with increasing concentrations of anti-α5β1 antibodies for 30 min, followed by incubated cells with BSA-S200 for 8 h in serum-free medium. The cell viability results indicated that pre-treatment of T47D cell lines with anti-α5β1 antibodies attenuated the cytotoxic effect of BSA-S200 (FIG. 3C). These data suggest that fibrillar proteins are cytotoxic to cancer cells by modulating Akt signaling pathway.

Effect of rgd motif and molecular weight of fibrillar proteins on cytotoxicity of cells. RGD motif is a ligand for integrins. It has been shown that fibrillar proteins induced cell death via modulating integrin/Akt signaling pathway. Fibronectin, a protein with an RGD motif and a molecular weight of 450 kD, also exhibited fibrillar structure when eluted from Superdex200 (FN-S200) in the presence of SDS (data not shown). The cytotoxicities of four fibrillar proteins i.e. rVP1-S200, FN-S200, rVP3-S200 and BSA-S200 on BHK-21 cells were compared (FIG. 4A). It has been found that fibrillar proteins with RGD motifs, like rVP1-S200 and FN-S200, were more cytotoxic than those without RGD motifs such as BSA-S200 and rVP3-S200. In addition, fibrillar proteins with higher molecular weight were more cytotoxic than those with lower molecular weight. FN-S200 (MW=450 kD) exhibited more cytotoxicity than that of VP1-S200 (MW=26 kD) (FIG. 4A). BSA-S200 (MW=66 kD) displayed more cytotoxicity than that of VP3-S200 (MW=26 kD) (FIG. 4 A). Although VP3-S200 did not show any cytotoxicity at the concentration of 0.5 µM as shown in FIG. 4A, higher concentrations of VP3-S200 did induce cytotoxicity in a dose-dependent manner (FIG. 4B). Taken together, fibrillar proteins with a RGD motif and higher MW possess more cytotoxicity to cells than those without RGD motif and with lower molecular weight.

In vitro and in vivo studies of fibrillar protein rVP1 as anti-cancer agent. Recombinant VP1 (rVP1) is more effective than doxorubicin and taxol in inhibiting growth of cancer cells in vitro. The cytotoxic effect of rVP1 in vitro was evaluated using MTT reagents. The IC50 values of rVP1 were much lower than that of doxorubicin in four different lung cancer and an ovarian cancer cell lines, including A549, H146, H23, H23/0.3, and SK-OV-3 cells, as well as a normal lung fibroblast cell line, WI-38. Higher inhibitory effect was also seen in SK-OV-3 cells treated with rVP1 compared to treatments of doxorubicin and taxol. The IC50 value of rVP1 for BNL cells was lower than that for AML 12 cells, a normal murine hepatocyte cell line, indicating that rVP1 was more cytotoxic to murine HCC cells than to normal hepatocytes.

Treatments of rVP1 inhibit tumor growth and extend survival of mice with HCC. BNL cells were injected subcutaneously into BALB/c mice and a tumor volume of 250 mm$^2$ was detected approximately two weeks after tumor induction. Four groups of mice were given intratumoral injection of rVP1 (25 mg/kg, 75 mg/kg, or 100 mg/kg) or PBS thrice weekly for three weeks. Mice treated with rVP1 had tumor volumes much smaller than that of untreated mice, with higher dosages of rVP1 showing more potent effect. The difference in tumor volume between control and treatment groups was statistically significant (25 mg/kg, P<0.05; 75 mg/kg and 100 mg/kg, P<0.001).

In another similar experiment with only two groups of mice, the tumor volumes of mice treated with rVP1 (75 mg/kg) were also much smaller than that of control mice receiving PBS. The median survival of mice treated with rVP1 or PBS was 11.5 and 13.5 weeks, respectively. Difference in survival between the two groups was calculated by log-rank test, and the result was statistically significant.

Treatments of rVP1 increase survival rate of nude mice with human ovarian tumors. Treatments of rVP1 were performed by 2-stage intraperitoneal injections. Nude mice with human ovarian tumor received first injection four hours after ascites induction with ip injection of SK-OV-3 cells, and different dosages of rVP1 (15, 50, 150 mg/kg) were injected every 48 hours for 10 times. Treatments were resumed after 10-day suspension, and injections of rVP1 were repeated every 48 hours for 5 times. Mice receiving rVP1 injections (15 and 50 mg/k/g) had higher survival rates compared to control mice.

Discussion

The method commonly used for preparation of amyloid fibrils is aging at 37° C. for a period of time. Most of the cases, it takes days to weeks for aging. Reports have shown that fibril formation can be accelerated by SDS; however it still needs vigorous stirring for overnight at 37° C., 2 days of incubation at room temperature, or with the assistance of fibril seeds. Moreover, all of these methods belong to batch-type production.

In the present study, a column is developed process which promotes fibrillar protein formation in the presence of detergent (SDS or Zwittergent 3-14) without fibril seeds (FIGS. 1A, D, and E; 2 A and B). Also, by using this column process, globular proteins are converted into fibrillar forms in a rapid, steady, efficient, and continuous manner. In addition, this process is also prone for scale-up. Previous studies has demonstrated that numerous proteins with diverse structures, including both disease and nondisease associated proteins, are capable of forming amyloid. A variety of proteins have been found with different sequences and structures that could be applied to this column chromatography process and converted into fibrillar proteins, for examples, BSA-S200, rVP1-S200, rVP3-S200 and FN-S200 (FIGS. 1A, D, and E). To reveal the optimal conditions of column-induced fibril formation, a study was conducted regarding some factors that might affect the fibril formation in this process.

Results suggested bead pore size plays a crucial role in the column-induced fibril formation. Superdex-200 column has a bigger bead pore size than that of Superdex-75 column (Table 1). An explanation as to why Superdex 75 column could not promote fibril formation (FIG. 1B) is that the limited bead pore size constrains the proteins from entering the bead matrix, thus leading to the lack of mechanical forces which might contribute to cause protein unfolding/folding and enhance fibrillogenic ensemble. Taken together, it is determined that mechanical force and detergent plays a role in the column-induced fibril formation.

Integrins are a family of integral membrane receptors that function as cell adhesion molecules. Each integrin is a heterodimer formed by the non-covalent association of α- and β-subunits. In mammalian species, the integrin family consists of 24 different heterodimers, each of which has a distinct tissue distribution. Integrins contribute to a variety of process, including adhesion between cells and the extracellular matrix and induction of signal transduction pathways that modulate various processes, including cell proliferation, morphology, migration, and apoptosis.

Previous studies have demonstrated amyloid fibrils are cytotoxic to neuron cells. Previous studies also demonstrated that α2β1 and αVβ1 integrin signaling pathways mediate amyloid-β-induced neurotoxicity. In this study, it was found that fibrillar proteins induced cancer cell death by modulating integrin α5β1 (FIGS. 3B and 3C). Integrin signaling can activate the Akt pathway.

Amyloid, regardless of source, is cytotoxic to neuron cells. The mechanism of amyloid-induced cytotoxicity may be related to interaction of amyloid-forming peptides with lipid membranes. However the cytotoxic effect of fibrillar protein on cancer cell has not been reported. We found that SDS assisted column-induced fibrillar proteins displayed cytotoxicity in human cancer cell lines (FIG. 3 C). BSA-S200 resulted in 70% reduction of cell viability at the concentration of 2 μM in T47D cell lines (FIG. 3 C).

Finally, the cytotoxic effects of fibrillar proteins with an RGD motif were compared with those without an RGD motif. RGD motif is a ligand for integrins that modulates a lot of functions such as cell migration, adhesion, or proliferation. The results suggested that fibrillar proteins with RGD motifs displayed more cytotoxicity to cells as compared to those of fibrillar proteins without RGD motifs (FIG. 4 A). It was also found that molecular weight of fibrillar protein plays a role in cytotoxicity induced by fibrillar proteins (FIG. 4 A).

Example 2

Materials and Methods

Materials. The antibodies against phospho-Try$^{576/577}$ FAK, phospho-Ser$^{473}$ Akt, and phospho-Ser$^9$ GSK-3β were purchased from Cell Signaling Technology (Beverly, Mass., USA). The antibody against phospho-Tyr$^{397}$ FAK was obtained from Biosource (Camirillo, Calif., USA). Zwittergent 3-14 was purchased from Calbiochem (San Diego, Calif., USA). Integrin α5β1 protein, anti-β-actin antibody, anti-integrin α5 antibody, anti-integrin α5β1 antibody (function-blocking antibody), horseradish peroxidase-coupled anti-mouse IgG secondary antibodies, horseradish peroxidase-coupled anti-rabbit IgG secondary antibodies, and MTT assay kit were purchased from Chemicon (Temecula, Calif., USA). Anti-BSA antibody was obtained from Molecular Probes (Eugene, Oreg., USA), BSA was purchased from Bio Basic Inc. (Canada). Aβ$_{25-35}$, purchased from Sigma (St. Louis, Mo., USA), was dissolved in sterile double-distilled water and aged at 37° C. for 3 days before use. Thioflavin T (ThT), sodium dodecyl sulfate (SDS), 4', 6'-Diamidino-2-phenylindole dilactate (DAPI), and other chemicals if not otherwise specified were obtained from Sigma (St. Louis, Mo., USA). Superdex-200, Superdex-75 beads were obtained from Amersham Biosciences (Uppsala, Sweden), HW55S gel filtration bead was obtained from TOSOH Corporation (Shiba, Tokyo, Japan).

Preparation of fibrillar BSAs (F-BSA). Twenty milligrams of BSA (Bio Basic Inc.) was dissolved in 10 ml of PBS with 1% SDS (w/v). The BSA solution was sonicated for 5 min, and subsequently applied to a Superdex-200, or a HWS55 column (2.6 cm×100 cm), which was previously equilibrated with a buffer solution (25 mM Tris-HCl, pH 8.0, 1 mM EDTA, 0.1 M NaCl, and 0.05% SDS). Fractions containing BSA were pooled. The pooled fractions were then dialyzed against PBS to remove SDS.

Transmission electron microscope (TEM). For Transmission electron microscope (TEM) analyses of fibrillar proteins, 1 mg/ml of proteins were applied to 200-mesh carbon-coated copper grids. Excess samples were removed and the grids were air-dried. The protein-bearing grids were negatively stained with 1% (W/V) phosphotungstic acid for 1 min. Transmission electron micrographs were observed at 20,000-150,000× magnification at 75 kV on a Hitachi H-7000 electron microscope.

Thioflavin T (ThT) fluorescence. For fluorescence measurements, increasing concentrations of proteins (10 μM, 20 μM, and 40 μM) were incubated with 20 μM ThT. After 1 h of incubation at room temperature, fluorescence was measured in triplicate on a Wallac VICTOR$^2$ 1420 Multilabel Counter (Perkin Elmer life science). Excitation and emission wavelengths were 430 nm and 486 nm, respectively. ThT background signal from buffer was subtracted from corresponding measurements.

Cell lines and treatments. BHK-21 cells (from hamster kidney; ATCC CRL-1632) and T47D cells (human breast duct carcinoma; ATCC HTB-133) were maintained at 37° C. in Dulbecco's modified Eagle's medium (DMEM) supplemented with 10% fetal bovine serum (FBS), 2 mM L-glutamine, 100 units/ml penicillin, and 100 μg/ml streptomycin. In brief, cells were seeded 24 hours prior to treatment. The cells were washed twice with PBS and incubated with proteins in serum-free DMEM for indicated time Cells were then lysed with 0.2 ml of lysis buffer (Pierce) at the indicated time points, and 30 μg of cell lysate was analyzed for FAK, Akt, and GSK-3β phosphorylation by Western blotting.

Cell survival assay. Cell survival was determined by MTT colorimetric assay. Exponentially growing cells (1×10$^4$ for BHK-21 cells; 1.25×10$^4$ for T47D cells) were seeded in 98-well plates in DMEM with 10% FBS and incubated for 24 h. Treatment of cell with a series of concentrations of proteins was carried out in serum-free DMEM for 8 h at 37° C. After treatment, the MTT solution was added to each well (0.5 mg/ml), followed by 4 h incubation. The viable cell number is directly proportional to the production of formazan which, following solubilization with isopropanol, can be measured spectrophotometrically at 560 nm in an ELISA plate reader.

SDS-PAGE and Immunoblot analyses. Cell lysates were resolved by 10% SDS-PAGE in Hoefer vertical gel apparatuses (Amersham Biosciences), followed by electrophoretic transfer to polyvinylidene difluoride membranes (Pall Corporation). The membranes were blocked with 5% skimmed milk powder in 5 mM Tris-HCl, pH 7.4, 136 mM NaCl, 0.1% Tween-20 (TBST buffer) for 1 h, and incubated with primary antibody (5-10 μg/ml) in blocking buffer. The membranes were then washed in TBST, followed by incubation with horseradish peroxidase-conjugated secondary antibody (Chemicon). The antibodies were detected with chemiluminescence (SuperSignal West Pico, Pierce) by exposure to Biomax ML film (Eastman Kodak).

Immunoprecipitation assay. Equal volumes (20 μl) of protein A/G beads (Santa Cruz Biotechnology) were pre-coated with or without integrin α5β1 protein by anti-integrin α5β1 antibody. The resultant beads were then incubated with either globular BSA (G-BSA) or fibrillar BSA (F-BSA) overnight at 4° C. After incubation, the immunocomplexes were washed three times with PBS and revealed by immunoblotting with anti-integrin α5 and anti-BSA antibodies.

Caspase-3 activity assay. Caspase-3 activity was determined by the cleavage of the fluorometric substrate z-DEVD-AMC (Upstate Biotechnology) according to the manufacturer's instructions. In brief, cells were harvested and washed twice in PBS, and lysed in a lysis buffer (Pierce) supplemented with protease inhibitor mixture (Sigma). The lysates underwent centrifugation at 12,000×g for 15 min at 4'C, and protein concentrations in the supernatants were determined by use of Bio-Rad Protein Assay. An amount of 50 μg of the cell lysates were incubated with 72 μM z-DEVD-AMC at room temperature for 15 min in triplicate. Cleavage of z-DEVD-AMC was determined by measurement of emission at 460 nm after excitation at 380 nm with the fluorescence plate reader.

Figures

Figure 5:
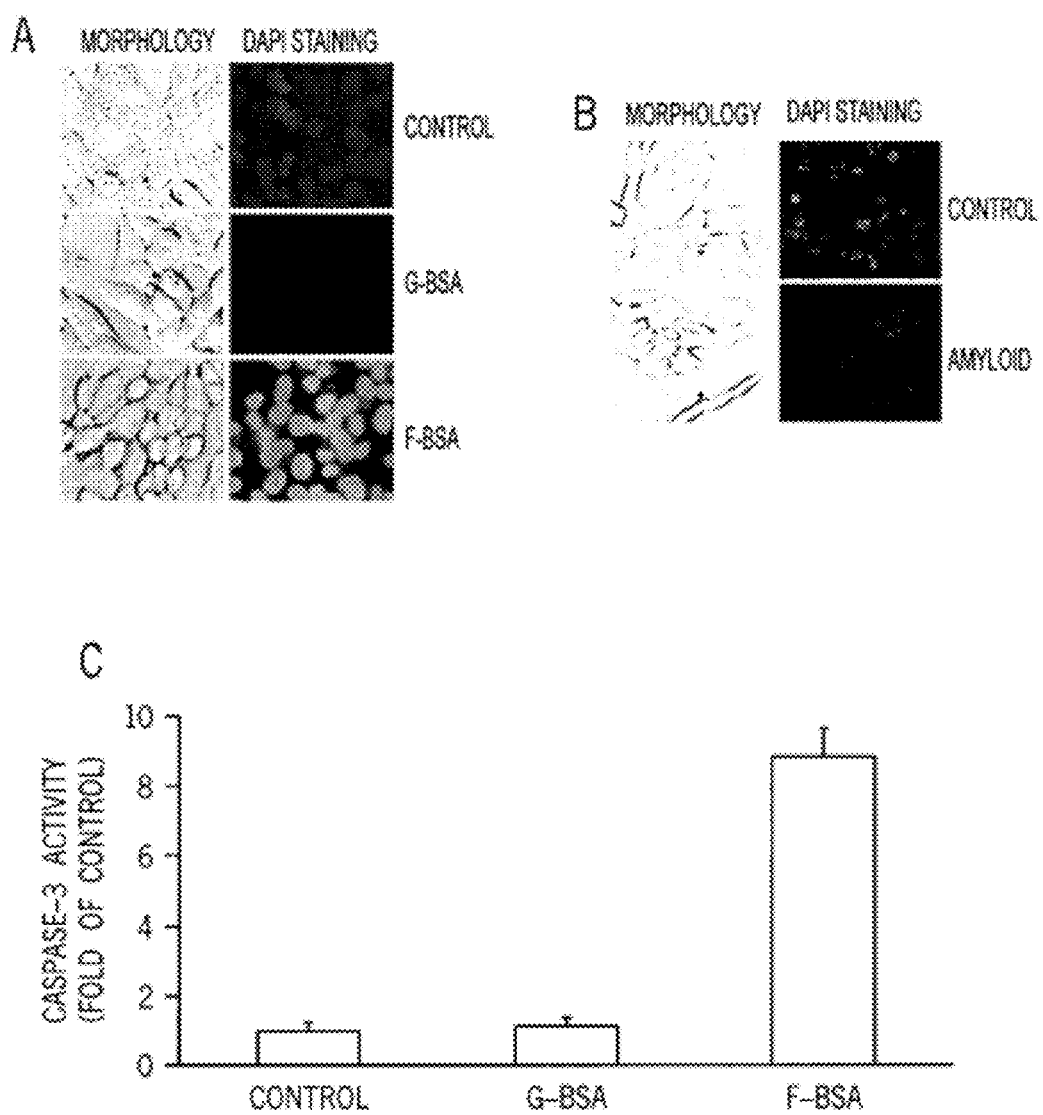

FIG. 5. Apoptotic effect of fibrillar BSA. (A) BHK-21 cells were incubated with 1 μM G-BSA (BSA) or F-BSA (BSA-S200) for 3 h. The cells were observed under a fluorescence microscope, and their nuclei were stained with DAPI (magnification in all panels, ×400). (B) BHK-21 cells were incubated with 40 μM $A\beta_{25-35}$ for 3 h. The cells were observed under a fluorescence microscope, and their nuclei were stained with DAPI (magnification in all panels, 400). (C) BHK-21 cells were cultured with 0.8 μM G-BSA or F-BSA for 15 h in serum free medium, then, subjected to caspase-3 activity analysis. The caspase-3 activity was measured by fluorogenic substrate as described under *Materials and Methods*. Data represent the mean±SD of three experiments.

Figure 6:
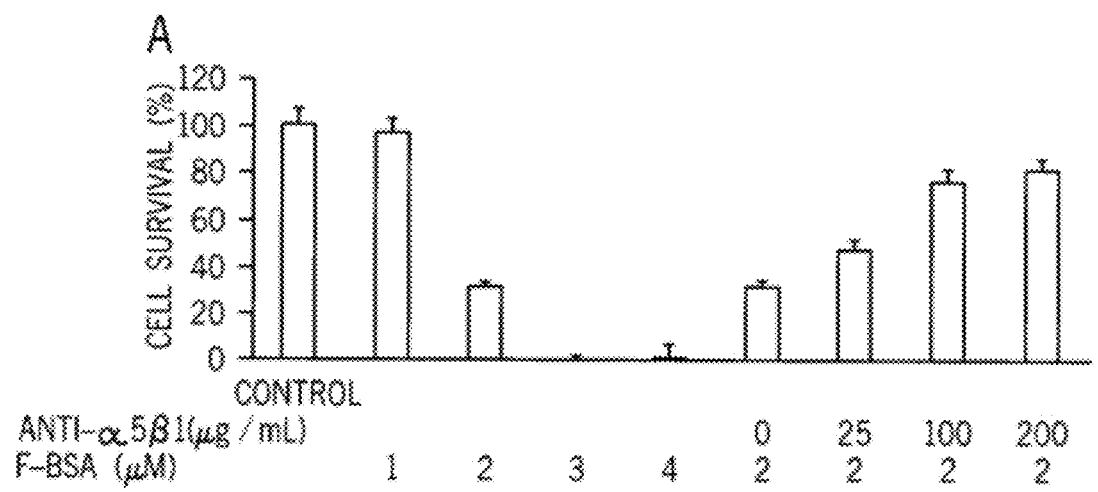
Figure 6:
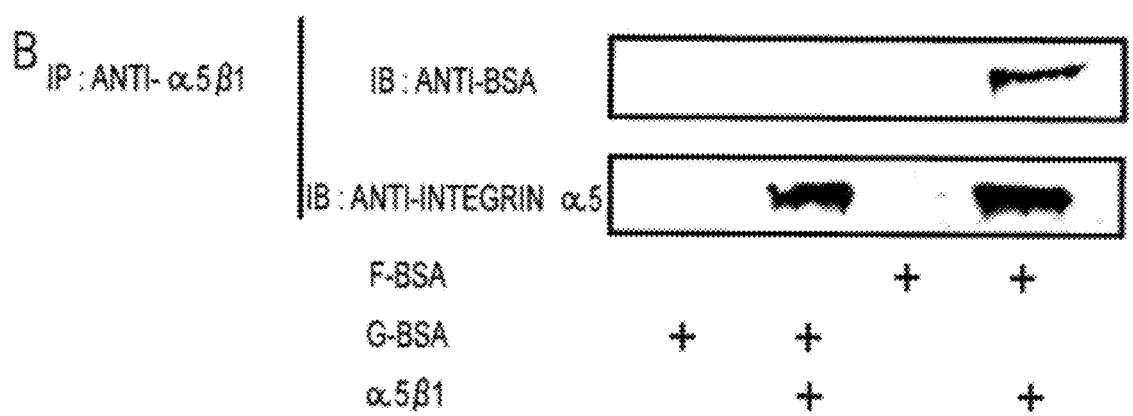

FIG. 6. Interaction Between Fibrillar BSAs (F-BSA) and Integrin α5β1. (A) T47D cell lines were pre-treated with or without anti-integrin α5β1 antibody for 30 min, followed by treatment with various concentrations of F-BSA (BSA-S200) in serum-free medium for 8 h. After treatment, cell viability was determined by the MTT assay. Data represent means±S.D. (n=3). (B) Integrin α5β1 protein was linked to protein A/G beads by anti-integrin α5β1 antibody, and then incubated with F-BSA (BSA-S200) or native BSA (G-BSA) overnight. The immunocomplexes were separated by SDS-PAGE and immunoblotted (IB) with anti-integrin α5 and anti-BSA antibodies.

Figure 7:
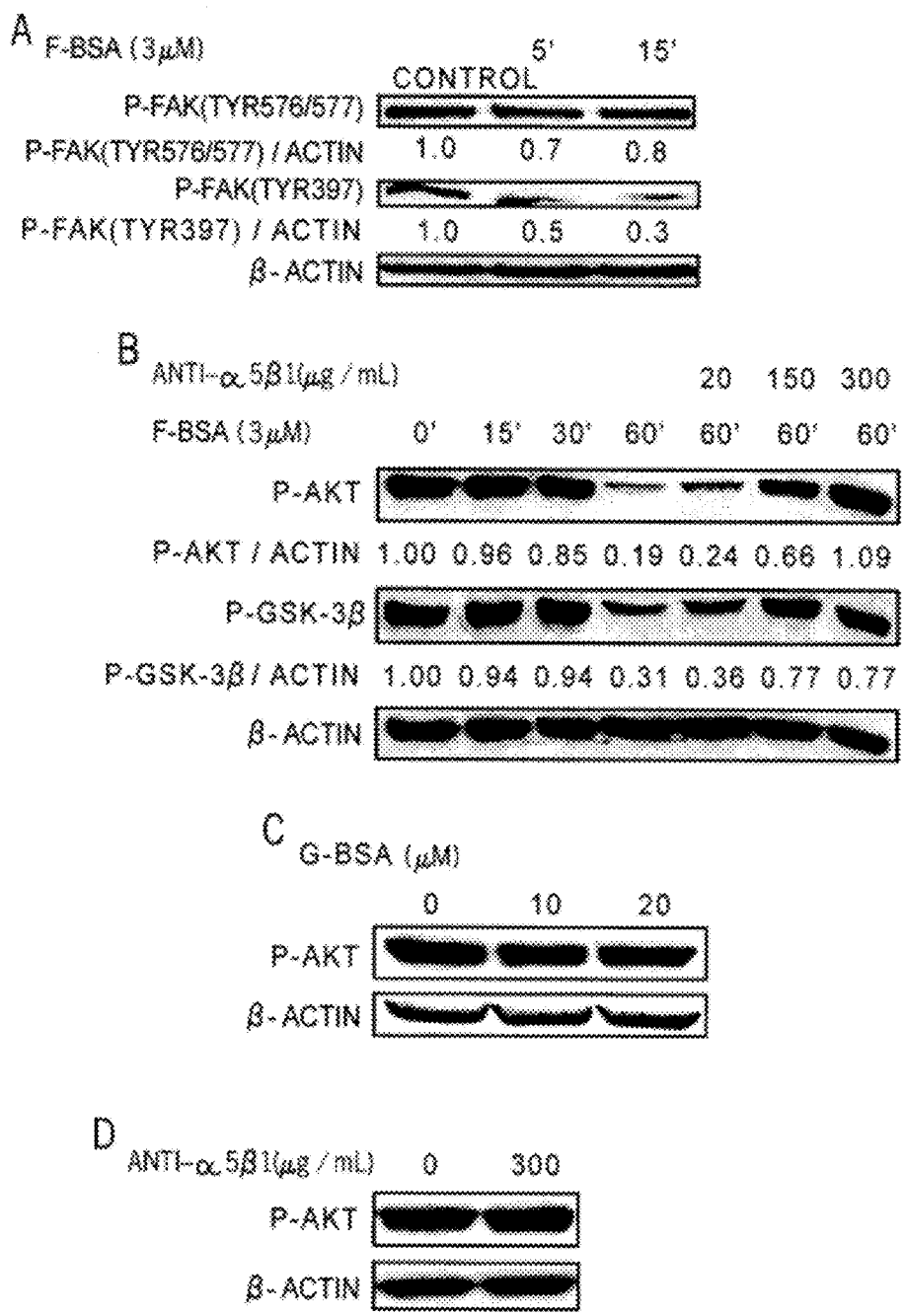

FIG. 7. Fibrillar BSA (F-BSA) induced cytotoxicity via the integrin/FAK/Akt pathway. (A) BHK-21 cells were treated with 3 μM F-BSA in serum-free medium for indicated time and cell lysates were analyzed by Western blotting using anti-phospho-FAK (Tyr576/577) or anti-phospho-FAK (Tyr397) as the primary antibodies, (B) BHK-21 cells were pre-treated with or without anti-integrin α5β1 antibody for 30 min, followed by treatment with 3 μM F-BSA in serum-free medium for indicated time. After treatment, cell lysates were analyzed by Western blotting using anti-phospho-Akt (p-Akt) and anti-phospho-GSK-3β (p-GSK-3β) as the primary antibodies, β-actin served as internal control for normalization purposes. (C) BHK-21 cells were treated with increasing concentrations of native BSA in serum-free medium for 1 h and cell lysates were analyzed by Western blotting using anti-phospho-Akt (p-Akt) as the primary antibody. (D) BHK-21 cells were treated with or without anti-integrin α5β1 antibody in serum-free medium for 1 h and cell lysates were analyzed by Western blotting using anti-phospho-Akt (p-Akt) as the primary antibody.

Results

Fibrillar BSA induced apoptosis in BHK-21 cells. To examine whether F-BSA-induced cytotoxicity is correlated with cellular apoptosis, DAPI staining and caspase-3 activity were measured. Results showed that fibrillar BSA induced nuclei condensation (FIG. 5A) and increased caspase 3 activity (FIG. 5C) as compared with BSA and amyloid (FIG. 5B). Taken together, these results suggest that F-BSA induces apoptosis of cells.

Fibrillar BSA induced apoptosis via integrin/FAK/Akt/GSK-3β pathway. In addition to BHK-21 cells, F-BSA was also cytotoxic to cancer cells such as T47D cells (a breast cancer line) as shown in FIG. 6A. To examine whether the apoptotic effects of F-BSA is via integrins that are known to modulate various processes such as cell proliferation, morphology, migration, and apoptosis, T47D cells were pre-treated with increasing concentrations of anti-α5β1 antibody for 30 min, followed by incubation with F-BSA (e.g. BSA-S200) for 8 h in serum-free medium. The cell viability results indicated that pre-treatment of T47D cells with anti-α5β1 antibody diminished the cytotoxic effect of F-BSA (FIG. 6A). The interaction between F-BSA and integrin was further verified by immunoprecipitation method. Incubation of control beads or integrin α5β1 protein-linked beads with BSA or F-BSA revealed that F-BSA but not BSA bound to integrin α5β1 (FIG. 6B).

It was then investigated whether the molecules involved in the cascade of integrin signaling pathway such as focal adhesion kinase (FAK), Akt and GSK-3β, are affected by F-BSA. Results showed that F-BSA dephosphorylated FAK at tyrosine position 397 (Tyr397) but not at position 576/577 FAK (Tyr576/577) in a time-dependent manner (FIG. 7A). Western blot also revealed that F-BSA dephosphorylated Akt as well as GSK-3β time dependently (FIG. 76). The effect of F-BSA on Akt and GSK-3β phosphorylation could be reversed by pre-treating the cells with increasing concentrations of anti-α5β1 antibody (FIG. 7B). In comparison, native BSA as well as anti-α5β1 antibody had no effect on the phosphorylation of Akt (FIGS. 7C and 7D). These results thus indicated that F-BSA induces apoptosis via an integrin/FAK/Akt/GSK-3β/caspase-3 pathway.

Discussion

Although native BSA is not a ligand for integrin (FIG. 6B), F-BSA caused cellular apoptosis by binding to integrin α5β1 (FIGS. 5 and 6). F-BSA mediates cell apoptosis by binding to integrin α5β1 leading to the dephosphorylation of FAK (Tyr 397), Akt and GSK-3β. F-BSAs produced in this study seem to deactivate integrin signaling pathway via a mechanism different from that induced by Aβ.

As BSA does not have RGD, a unique binding motif for integrin, the mechanism of binding of fibrillar BSA to integrin is likely not completely the same as molecules which has RGD in its sequence. Of note, even though some of the RGD containing peptides are cytotoxic, others such as fibronectin are not (Fornaro, et al. *Journal of Biological Chemistry* 278 (50): 50402-504011: 2003).

Example 3

Figure 8:
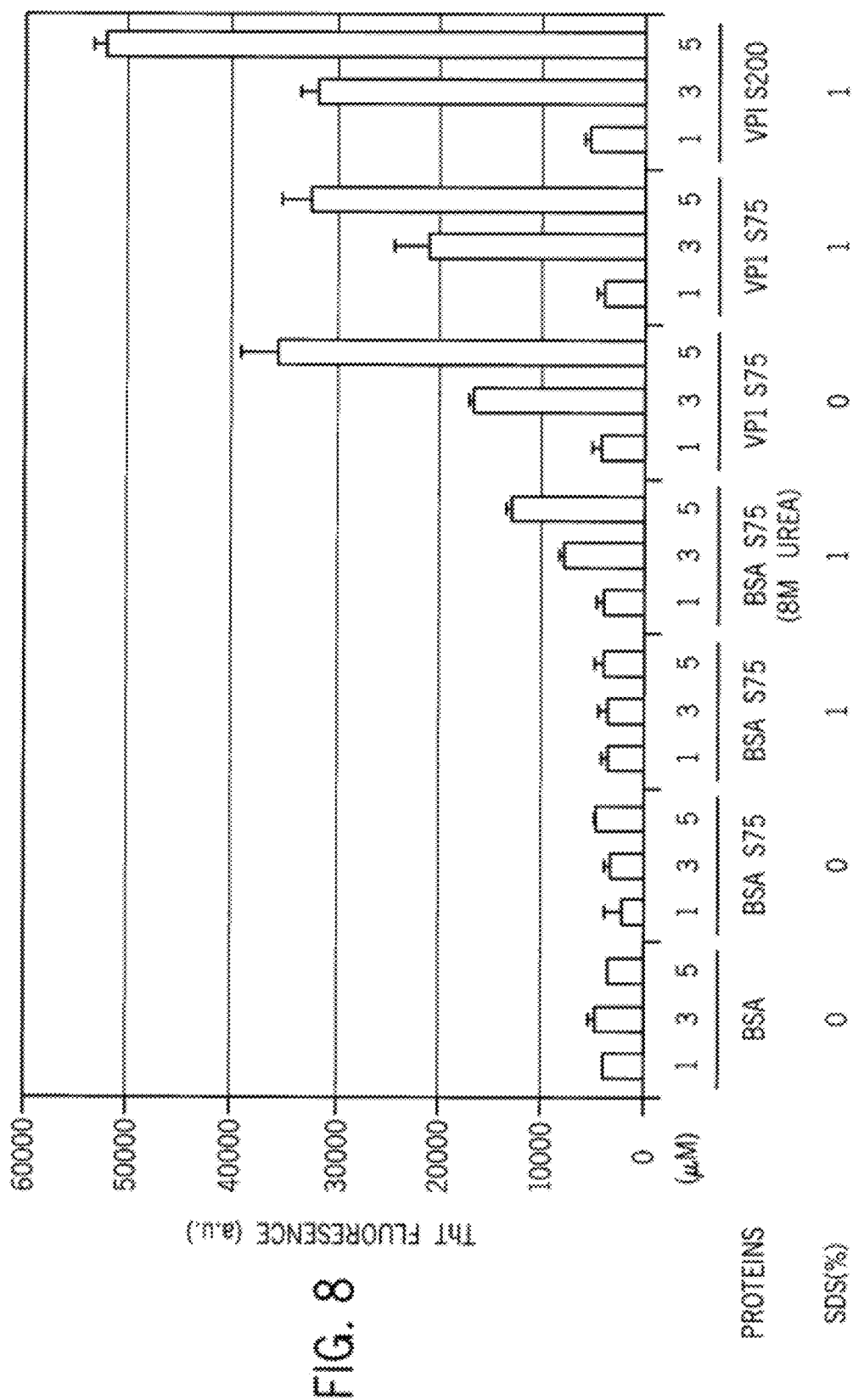
FIG. 8 is a graph illustrating the fluorescence levels of ThT in relation to different concentrations of various proteins.
Figure 9:
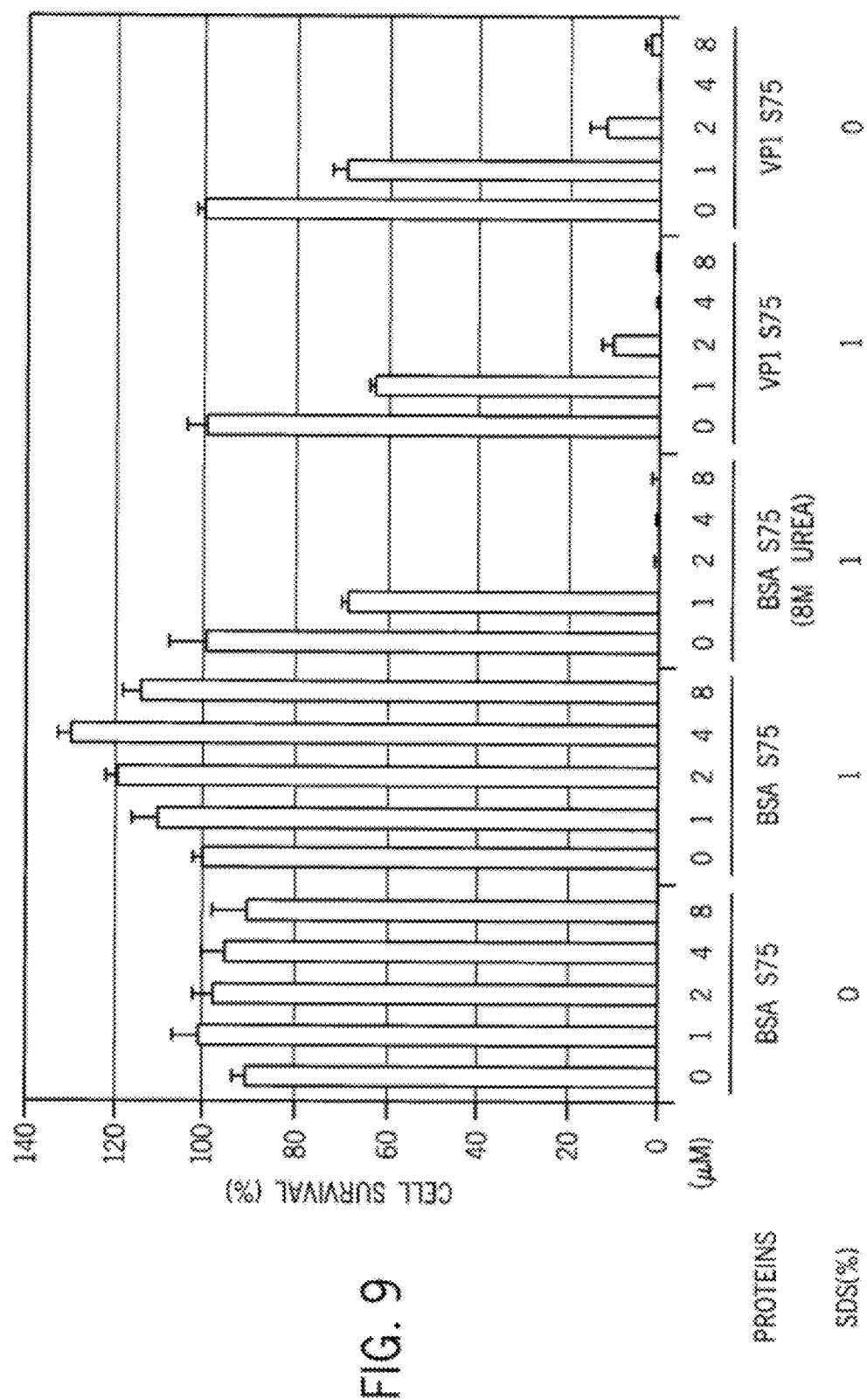
FIG. 9 is a graph illustrating cell cytotoxicity in relation to different concentrations of various protein preparations eluting from Superdex-75 column.

It was found that Superdex-75 induced unfolded BSA, in the presence of 8M urea, to have a fibril formation. Recombinant VP1 was also found to have a fibril formation induced by Superdex-75 and in the presence of about 8M urea. This was evidenced through enhanced ThT level (FIG. 8) and cytotoxicity (FIG. 9). The use of 8M urea is not a limitation, other molar ratios will promote unfolding to the same or a lesser degree.

Example 4

Materials and Methods

Materials. The antibody against TLR2 was obtained from Abcam. Anti-TLR2 monoclonal antibody (an antagonistic antibody) was purchased from eBioscience. Control IgG, fibronectin (FN), and horseradish peroxidase-coupled anti-rabbit IgG secondary antibodies were purchased from Chemicon. Bovine serum albumin (BSA) was purchased from Bio Basic Inc. Anti-BSA antibody was obtained from Invitrogen. Thioflavin T (ThT) and Sodium dodecyl sulfate (SDS) were purchased from Sigma.

Expression of VP3 in *E. coli*. VP3 is a component of capsid proteins of foot-and-mouth disease virus (FMDV). The VP3 gene was amplified by PCR from the plasmid pIBSY1-P1 (Yang, et al. *The Journal of Gene Medicine* 7:708-717: 2005) with 5'-CCGGGATCCAAGCTTGGGATTTCCCCGTGGCA-3' (SEQ ID NO: 1) and 5'-CCGCTCGAGTTGGGTTCGGGCGTCGAC-3' (SEQ ID NO: 2) as primers, which introduced a BamHI site at the N-terminus and an XhoI site at the C-terminus, respectively. To facilitate the purification and assay of the recombinant *E. coli* derived VP3, a T7 tag and His tag were attached to the N- and C-terminus of the VP3 gene, respectively. After restriction enzyme digestion, the amplified gene was ligated between the BamHI and the XhoI site of pET24a (+) (Novagene, Wis.) and transformed into DH5α competent cells. The identified positive clones were verified by sequencing. Plasmid pVP3, isolated from one of the positive clones, was used to transform *E. coli* BL21 (DE3) competent cells. Recombinant VP3 (rVP3) was purified after expression in *E. coli* according to the procedure described in Wang, et al. *Vaccine* 21:3721-3729: 2003.

Preparation of fibrillar proteins by column chromatography. For the preparation of BSA-S200 and FN-S200, 10 ml PBS-dissolved proteins (2 mg/ml) were prepared and SDS (10%; w/v) was subsequently added to the final concentration of 1%. After sonication for 5 min, the SDS-containing protein solution was subsequently applied to Superdex-200 column (2.6 cm×100 cm, Amersham Biosciences) or Superdex-75 column, which were previously equilibrated with a buffer solution containing 25 mM Tris-HCl, pH 8.0, 1 mM EDTA, 0.1 M NaCl, and 0.05% SDS. Fractions containing proteins were pooled. The pooled fractions were then dialyzed against phosphate-buffered saline (PBS) for 4.5 h (three times; 1.5 h/time) in order to remove SDS.

Transmission electron microscope (TEM). For transmission electron microscope (TEM) analyses of proteins with or without processing through column chromatography, equal amount of proteins were applied to 200-mesh carbon-coated copper grids. Excess samples were removed and the grids were air-dried. The protein-bearing grids were negatively stained with 1% (W/V) phosphotungstic acid for 1 min. Transmission electron micrographs were recorded at 20,000-150,000× magnification at 75 kV on a Hitachi H-7000 electron microscope.

Thioflavin T (ThT) fluorescence. For fluorescence measurements, increasing concentrations of proteins were incubated with 20 μM ThT. After 1 h of incubation at room temperature, fluorescence was measured in triplicate on a Wallac VICTOR$^2$ 1420 Multilabel Counter (Perkin Elmer life science). Excitation and emission wavelengths were 355 nm and 535 nm, respectively. ThT background signal from buffer was subtracted from corresponding measurements.

Cell lines. Murine macrophage cell line RAW 264.7 and human embryonic kidney cell line (HEK 293T) were maintained at 37° C. in Dulbecco's modified Eagle's medium (DMEM) supplemented with 10% fetal bovine serum (FBS), 2 mM L-glutamine, 100 units/ml penicillin, and 100 μg/ml streptomycin in a humidified atmosphere containing 5% $CO_2$.

SDS-PAGE and immunoblot analyses. Samples were separated on 10 or 12% SDS-PAGE gels in Hoefer vertical gel apparatuses (Amersham Biosciences), followed by electrophoretic transfer to polyvinylidene difluoride membranes (Pall Corporation). The membranes were blocked with 5% skimmed milk powder in PBST for 1 h, and incubated with primary antibody (5-10 μg/ml) in blocking buffer. The membranes were then washed in PBST, followed by incubation with horseradish peroxidase-conjugated secondary antibody (Chemicon). The antibodies were detected with chemiluminescence (SuperSignal West Pico, Pierce) by exposure to Biomax ML film (Eastman Kodak).

Immunoprecipitation assay. RAW 264.7 cells were lysed in cold lysis buffer (Pierce) supplemented with protease inhibitor mixture (Sigma-Aldrich). Equal amount of protein A/G beads were precoated with or without rVP3-S200. The beads were then incubated with RAW 264.7 cell lysate overnight at 4° C. The resultant beads were collected by centrifugation and washed three times with cold lysis buffer. Proteins from immunocomplexes were eluted by boiling in SDS sample buffer and analyzed by SDS-PAGE and immunoblotted with a specific antibody.

Immunofluorescence and confocal microscopy. Subconfluent monolayers of RAW 264.7 cells, grown on 12-mm glass coverslips in 24-well tissue culture dishes, were treated with BSA or BSA-S200 for 1 h at 4° C. in Dulbecco's modified Eagle's medium (DMEM) without fetal bovine serum (FBS). After treatment, the monolayers were washed with PBS and fixed with 4% paraformaldehyde. After fixation, the paraformaldehyde was removed and the monolayers were incubated with the primary antibodies for 1 h at room temperature. When double labeling was performed, cells were incubated with both antibodies together. The dilutions of the primary antibodies were as follows: anti-TLR2 (1/100) and anti-BSA (1/200). After being washed three times with PBST, the cells were incubated with the appropriate secondary antibody conjugated with fluorescence, goat anti-rabbit IgG (1/500; Alexa Fluor 488; Molecular Probes) or goat anti-mouse IgG (11500; Alexa Fluor 555; Molecular Probes) for 30 min at room temperature. Following this incubation, the coverslips were washed three times with PBST, mounted, and examined on a LSM 510 META confocal microscope.

Luciferase reporter gene assay. Human TLR2 was transiently expressed in human embryonic kidney (HEK293T) cells and then assayed for their responsiveness to samples. HEK293T cells were transfected with pRK-FLAG-TLR2 which contains the human TLR2 gene or pcDNA3.1 as empty vector control; pNFkB-Luc, which contains a luciferase reporter gene regulated by the NF-kB binding sequence. The luciferase gene is expressed only when NF-kB binds to the binding sequence. To normalize for transfection efficiency, the cells were cotransfected with pcDNA3.1-β-gal. Plasmids were introduced into HEK293T cells by transfection using Lipofectamine2000 (Invitrogen). Briefly, HEK293T cells were cultured in a 96-well plate at a concentration of $2.5\times10^4$ cells per well in 0.1 ml Dulbecco's modified Eagle's medium (DMEM) supplemented with 10% heat-inactivated fetal bovine serum (FBS), 100 units/ml penicillin and 100 μg/ml streptomycin sulfate at 37° C. overnight. Medium was replaced by Opti-MEMI (Invitrogen) just before transfection. The Transfection mixture was prepared by diluting 0.3 μl of Lipofectamine2000 in 25 μl of OPTI-MEMI medium to which 0.1 μg of plasmid DNA (0.01 μg well pRK-FLAG-hTLR2 or pcDNA3.1 as empty vector, 0.07 μg/well p5xNFkB-luc reporter plasmid (Stratagene) and 0.02 µg/well pcDNA3.1-βgal) in 25 µl of OPTI-MEMI was then added after a 20 minutes incubation at room temperature. The DNA-Lipofectamine2000 mixture was then added to the cells and mixed by gently shaking. After 24 hours of incubation at 37° C. in 5% CO2, the cells were stimulated with samples. As positive controls, cells were stimulated with the TLR2 ligand Pam3CSK4 (InvivoGen). After 6 hours, cells were lysed and assayed for luciferase activity using the luciferase assay system (Promega) according to the manufacturer's instructions. Cells were washed twice with 100 µl of PBS and lysed in 100 µl of passive lysis buffer (Promega). Twenty µl cell lysate was used to measure luciferase activity. The luciferase activity of each sample was normalized to the β-galactosidase activity. Experimental data were expressed as the fold increases over those of unstimulated control cells transfected with empty vector.

Cytokine quantification by ELISA. Transiently transfected HEK293T cells that expressed TLR2 as well as murine macrophage cell line RAW264.7 were stimulated for 6 or 24 hours respectively with TLR2-specific ligand or fibrillar proteins. Cell culture supernatants were collected and analyzed using cytokine-specific ELISAs (IL-6, IL-8 and TNF-α ELISAs from Biosource International), performed according to the manufacturer's protocol.

Figures

Figure 10:
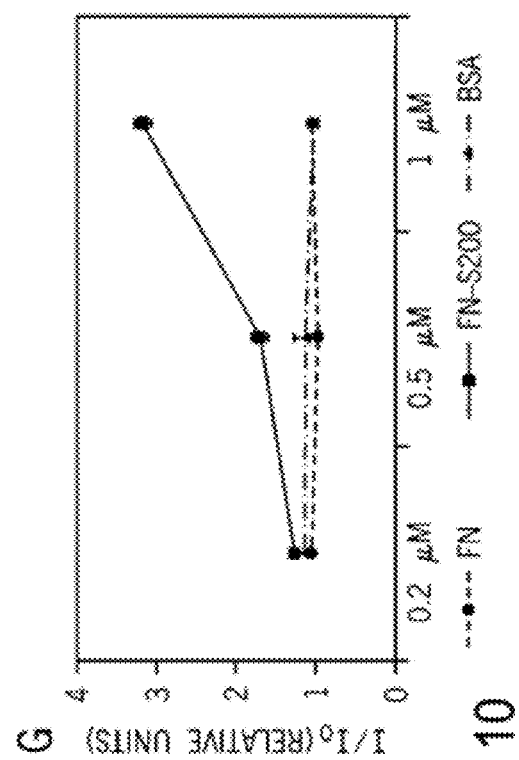
Figure 10:
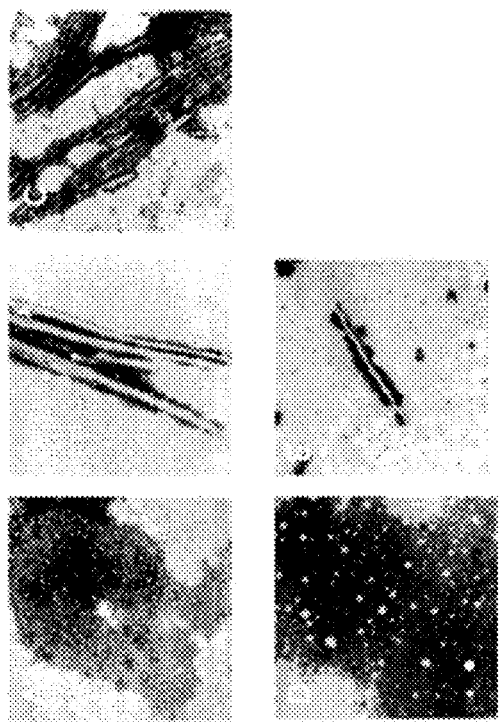
Figure 10:
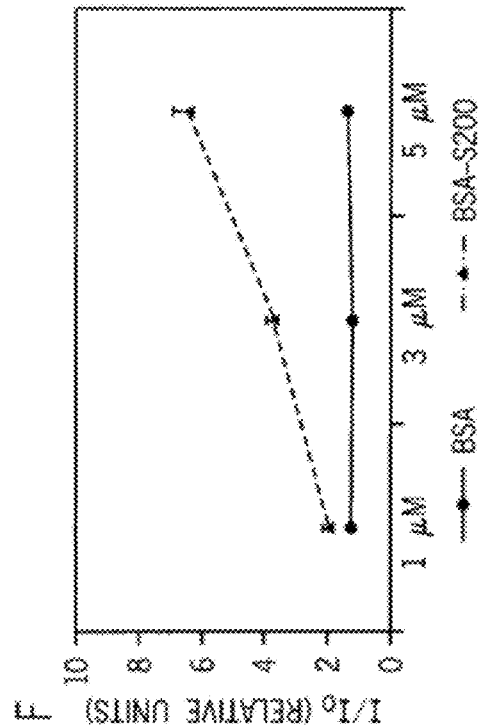

FIG. 10. Superdex-200 chromatography promotes the formation of fibrillar proteins. TEM images show fibrillar structures of BSA-S200, rVP3-S200, and FN-S200 prepared from superdex200 chromatography (B, C, and E). Natural forms of BSA and FN, which are as controls, show globular structure under TEM images (A and D). (F and G), incubation of BSA-S200 or FN-S200 with 20 µM amyloid-specific dye ThT results in enhanced fluorescence of ThT, when compared with natural forms of BSA or FN. The values are from three independent measurements. Data are shown as an average±SD from n=3.

Figure 11:
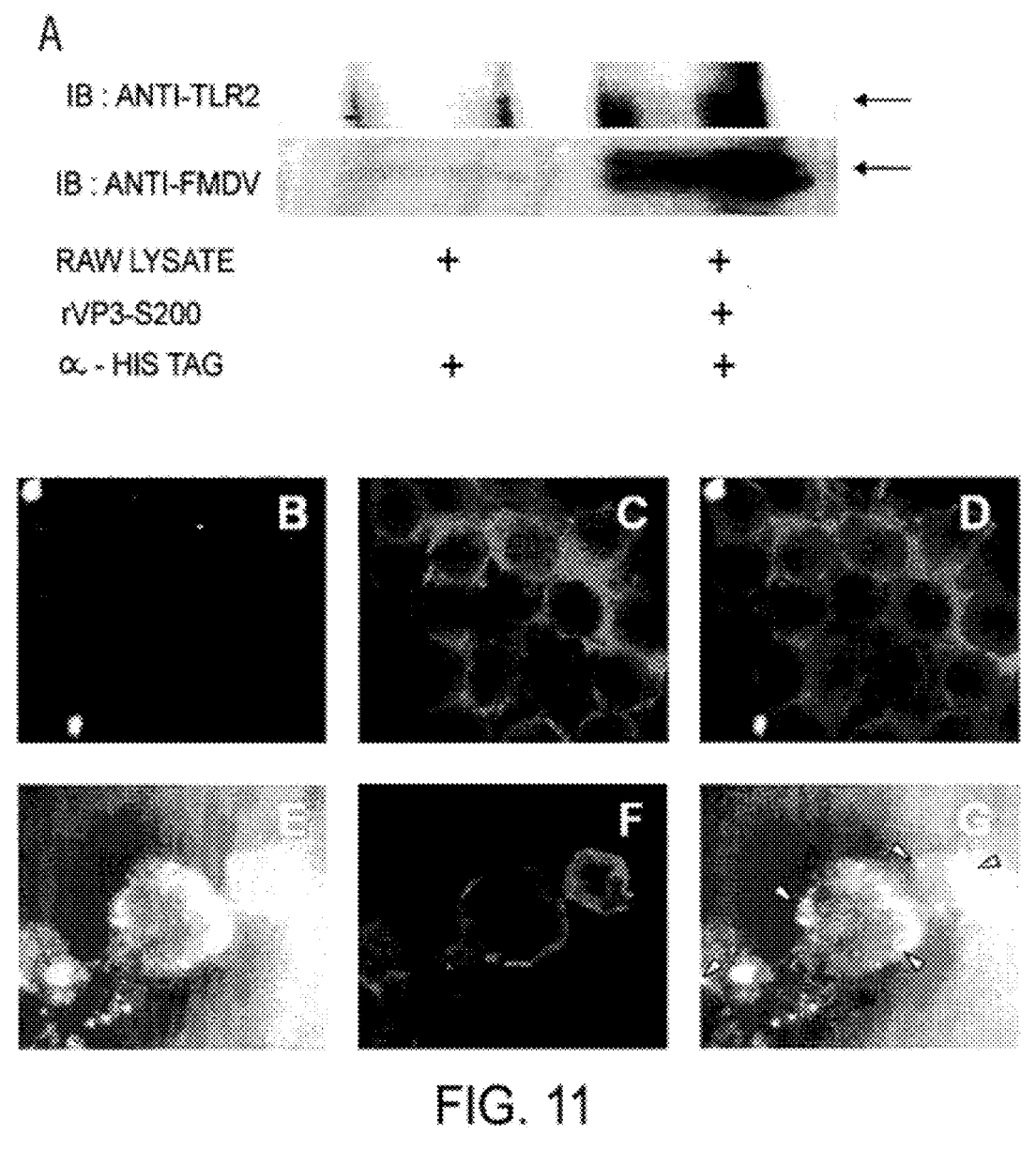

FIG. 11. Fibrillar proteins interact with TLR2. (A), Lysate from RAW 264.7 cells was incubated with rVP3-S200 immobilized on protein A/G beads or protein A/G beads alone for overnight; the protein A/G beads-bound proteins were separated by SDS-PAGE and immunoblotted with anti-TLR2 antibody or anti-FMDV antibody. BSA or BSA-S200 was adsorbed to RAW 264.7 monolayers at a concentration of 0.3 µM for 1 h at 4'C. The cells were processed for IF staining as described in *Materials and Methods*. BSA or BSA-S200 was stained with anti-BSA antibodies and visualized with Alexa Fluor 488 (green) (B and E), and the TLR2 was stained with anti-TLR2 antibodies and visualized with Alexa Fluor 555 (red) (C and F). Arrows in the merged image (G) point to some of the co-localized areas.

Figure 12:
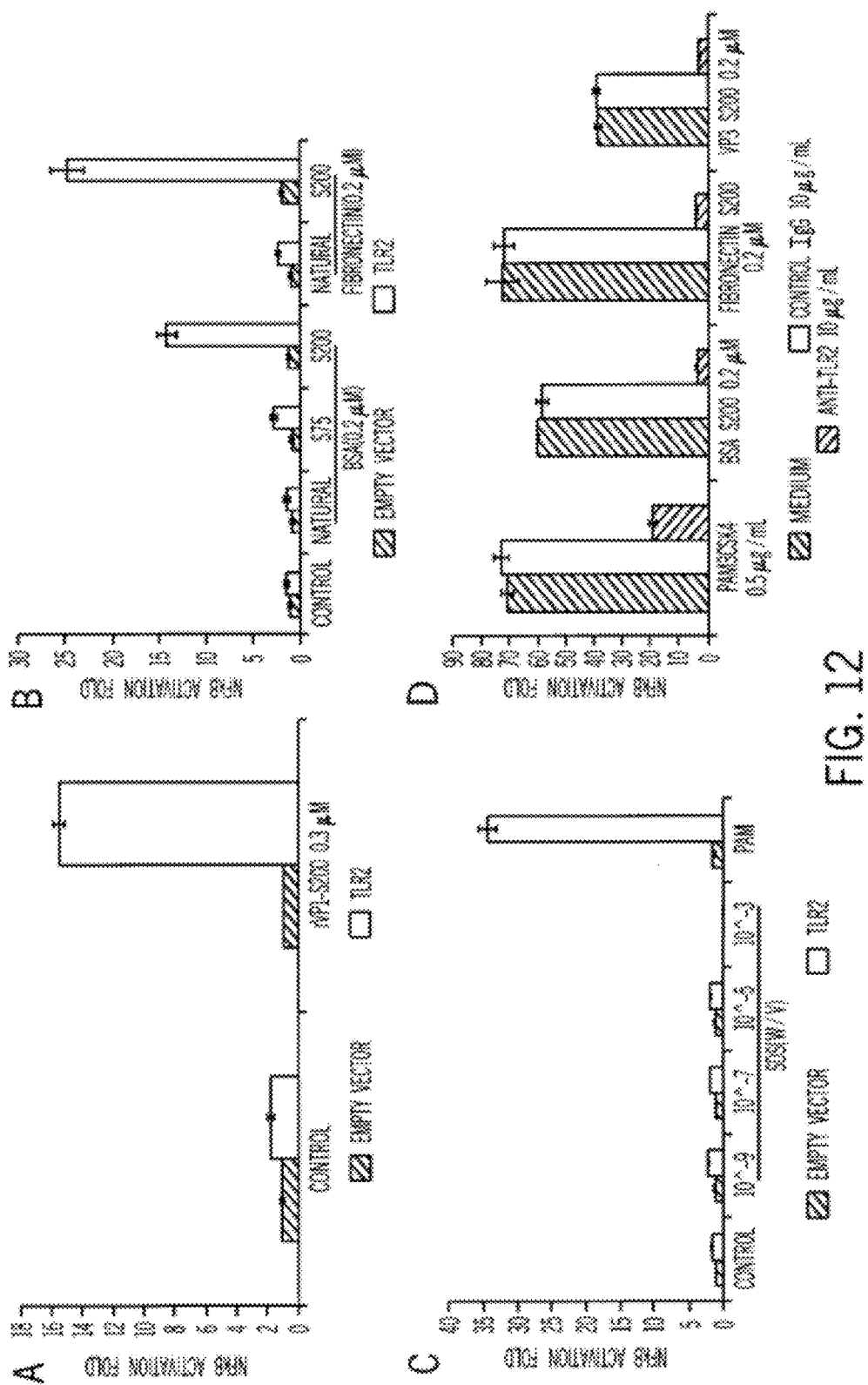

FIG. 12. Fibrillar proteins signal through TLR2. HEK293/TLR2 cells were stimulated with (A) 0.3 µM rVP1; (B) 0.2 µM BSA, BSA-S200, FN, or FN-S200. After 6 h, the cells were lysed, and NFκB reporter luciferase levels were measured. (C), HEK293/TLR2 cells were stimulated with pam$_3$csk$_4$ (0.5 µg/ml) or increased concentrations of SDS. After 6 h, the cells were lysed, and NFκB reporter luciferase levels were measured. (D), HEK293/TLR2 cells were pretreated with 10 µg/ml neutralizing anti-TLR2 antibody or control IgG for 1 h. Cells were then incubated with pam$_3$csk$_4$ (0.5 µg/ml), BSA-S200 (0.2 µM), FN-S200, or rVP3-S200 (0.2 µM) After 6 h, the cells were lysed, and NFκB reporter luciferase levels were measured. The values are from three independent measurements. Data are shown as an average±SD from n=3.

Figure 13:
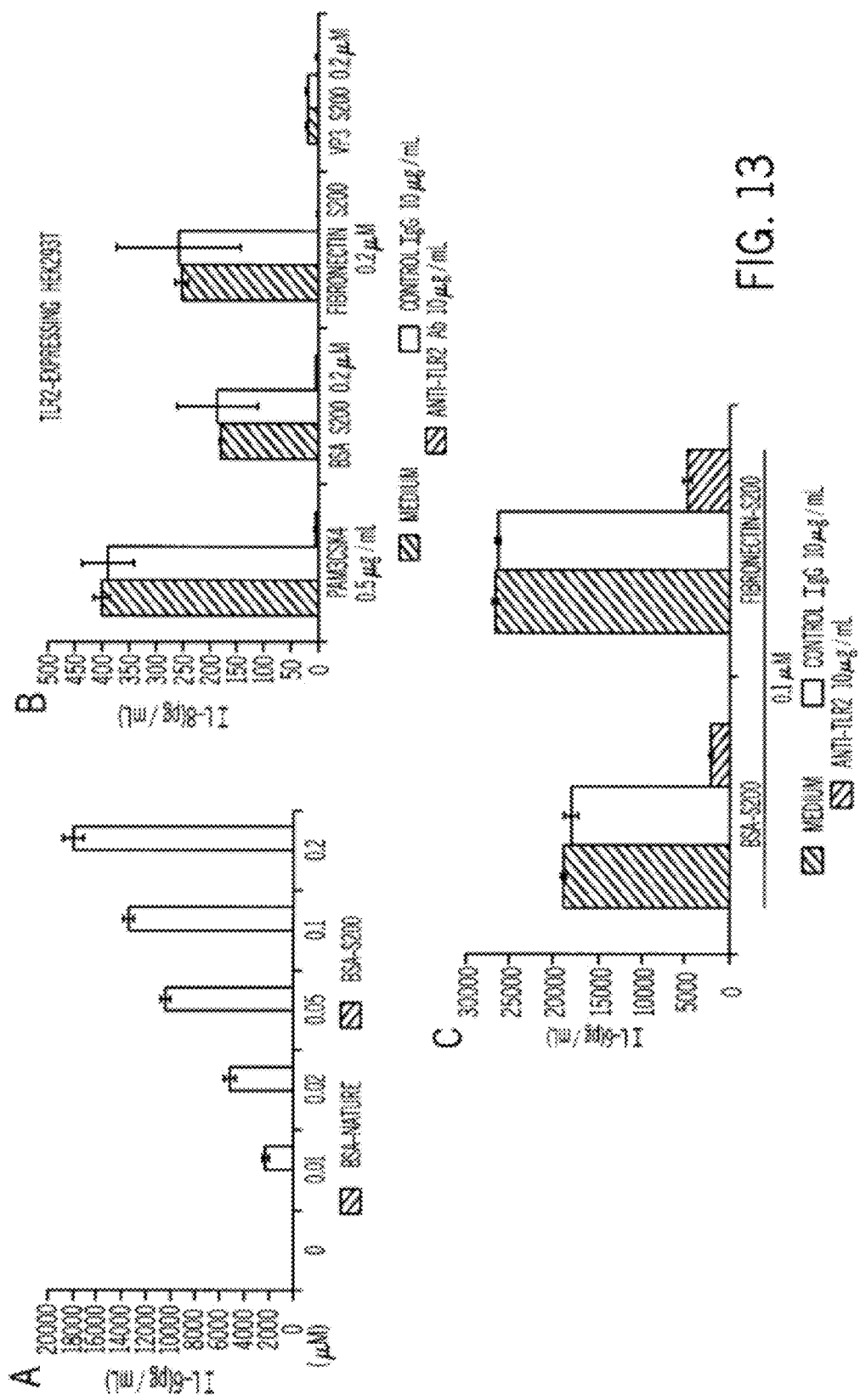

FIG. 13. Fibrillar proteins-induced cytokine production is through TLR2. (A), RAW 264.7 cells were incubated with different concentrations of BSA or BSA-S200. After 24 h, culture medium was analyzed for IL-6 using ELISA. (B), HEK293/TLR2 cells were pretreated with 10 µg/ml neutralizing anti-TLR2 antibody or control IgG for 1 h. Cells were then incubated with pam$_3$csk$_4$ (0.5 µg/ml), BSA-200 (0.2 µM), FN-S200 (0.2 µM), or rVP3-S200 (0.2 µM). After 6 h, culture medium was analyzed for IL-8 using ELISA. (C), RAW 264.7 cells were pretreated with 10 µg/ml neutralizing anti-TLR2 antibody or control IgG for 1 h. Cells were then incubated with BSA-200 (0.2 µM) or FN-S200 (0.2 µM). After 24 h, culture medium was analyzed for IL-6 using ELISA. The values are from three independent measurements. Data are shown as an average±SD from n=3.

Results

Proteins after passing Superdex-200 column exhibit amyloid-like fibrillar properties. To determine the structural characteristics of proteins after processing through Superdex-200 column, a transmission electron microscope (TEM) and Thioflavin T (ThT) assay were used. The TEM analyses revealed that BSA-S200, rVP3-S200, and FN-S200 showed fibrillar structure (FIGS. 10B, 10C, and 10E). On the contrary, natural form of BSA and FN exhibited spherical structure (FIGS. 10A and 10D). Next, the fluorescent emission of amyloid-like fibrils were examined with the specific dye ThT, which was incubated with the proteins. The data showed that BSA-S200 and FN-S200 enhanced fluorescent emission of ThT in a dose-dependent manner (FIGS. 10F and 10G).

Fibrillar proteins interact with TLR2. To analyze the binding of rVP3-S200 to TLR2 on RAW 264.7 cells, an immunoprecipitation protocol was used that exposed RAW cell lysates to rVP3-S200 coated beads or control beads. Incubation of rVP3-S200 linked beads but not control beads with RAW cell lysates revealed that rVP3-S200 bound to TLR2 (FIG. 11A). To further investigate whether BSA-S200 co-localized with TLR2, immunofluorescence-confocal microscopy was performed. BSA or BSA-S200 was added to RAW 264.7 cells at 4° C. for 1 h, and localization of BSA or BSA-S200 in relation to TLR2 was determined by confocal microscopy. Results suggested that BSA-S200 but not BSA co-localized with TLR2 (FIG. 11B-G).

Fibrillar proteins activate TLR2. Stimulation of human cells overexpressing TLR2 with rVP1-S200 (0.3 µM), BSA-S200 (0.2 µM) or FN-S200 (0.2 µM) resulted in the significant activation of NFκB, while globular form of BSA and FN did not (FIGS. 12A and 12B). To further investigate the specificity of TLR2, TLR2-expressed HEK293T cells were pretreated with anti-TLR2 antibody for 1 h, the cells were then stimulated with pam3csk4 (0.5 µg/ml), BSA-S200 (0.2 µM), FN-S200 (0.2 µM), or rVP3-S200 (0.2 µM). pam3csk4 is a known ligand for TLR2 and served as positive control. After 6 h incubation, cells were lysed and NFκB activation was determined. Pretreatment with anti-TLR2 significantly reduced NFκB activity while pretreatment with the isotype antibody control did not (FIG. 12D). Since SDS was used in the preparation of fibrillar proteins, the effect of SDS on TLR2 activation was also examined. The data revealed that SDS with increasing concentrations had no effect on the activation of TLR2 (FIG. 12C). Of note, BSA treated with SDS and eluted from a Superdex-75 column (BSA-S75) also showed a TLR2 activation effect but to a lesser degree than BSA-S200.

Release of cytokine induced by fibrillar proteins. RAW 264.7 cells were incubated with different concentrations of BSA or BSA-S200. After 24 h, culture medium was analyzed for IL-6 using ELISA. BSA-S200 but not BSA induced IL-6 production in a dose-dependent manner (FIG. 13A). To evaluate the involvement of TLR2 in the cytokine production, TLR2 blocking antibody was used for further study. Both HEK293T cells expressing TLR2 (FIG. 13B) and RAW 264.7 cells (FIG. 13C) were pretreated with anti-TLR2 antibody or control IgG for 1 h, followed by stimulation of cells with pam3csk4 (0.5 µg/ml), BSA-S200 (0.2 µM), FN-S200 (0.2 µM), or rVP3-S200 (0.2 µM) and measurement of IL-8 and IL-6 production. The presence of BSA-S200, FN-S200, and rVP3-S200 led to an increased level of IL-8 and IL-6 produced from TLR2-expressing HEK293T or RAW 264.7 cells. On the other hand, pretreatment of anti-TLR2 antibody but not control IgG significantly reduced the cytokine production (FIGS. 13B and 13C).

Discussion

Immunoprecipitation and immunofluorescence studies revealed that fibrillar proteins bound to TLR2 (FIG. 11). TLR2 is a member of toll-like receptors which mediate the cellular response to conserved molecular patterns shared by microorganisms. TLR2 recognizes varieties of ligands (Miyake. *Seminars in Immunology* 19:3-10: 2007; Kaisho, et al. *Biochimica et Blophysica Acta* 1589:1-13: 2002) and facilitates macrophage production of cytokine (Tsuji, et al. *Infection and Immunity* 68:6883-6890: 2000; Basu, et al. *The Journal of Biological Chemistry* 279:7370-7377: 2004). In this study, it was found that column-induced fibrillar proteins induced IL-6 production in RAW 284.7 cells in a dose-dependent manner (FIG. 13A). Pretreatment of RAW 264.7 (FIG. 13C) or TLR2 expressing HEK293T cells (FIGS. 12C and 13B) with anti-TLR2 antibodies diminished cytokine production induced by fibrillar proteins. These data suggest column-induced fibrillar proteins represent an agonist of TLR2 and induce cytokine release from immune cells.

Several studies have demonstrated toll-like receptors as adjuvant receptors (Hawkins, et al. *The Journal of Pharmacology and Experimental Therapeutics* 300:655-661: 2002). Freund adjuvant induces TLR2 expression in the liver of mice (Lim. *International Immunopharmacology* 3:115-118: 2003). TLR2 mediates the adjuvant activity of its ligand, lipoprotein (Ishii, et al. *Journal of clinical Immunology* 27:363-371: 2007). TLR2 and TLR4 are also involved in the immune response of BCG-CWS, constituents of mycobacteria as an effective immune adjuvant (Tsuji, at al. *Infection and Immunity* 68:6883-6890: 2000). This study is related to the findings of fibrillar proteins that induce cytokine production through activation of TLR2. The conversion of an antigen to fibrillar form increases the antigenicity of the antigen. Therefore, no added adjuvant is needed.

Among these TLRs, TLR2 recognizes a broad range of ligands, such as gram-positive cell walls (Yoshimura, at al. *J Immunol* 163:1-5: 1999), atypical lipopolysaccharides (LPS) (Bainbridge, at al, *Cellular Microbiology* 8:120-129: 2006; Reife, et al. *Cellular Microbiology* 8:857-868: 2006; Jotwani, et al. *European Journal of Immunology* 33:2980-2986: 2003), porins (Massari, at al. *J Immunol* 176:2373-2380: 2006; Singleton, et al. *J Immunol* 174:3545-3550: 2005), peptidoglycan (PGN) (Tsuji, at al. *Infection and Immunity* 68:6883-6890: 2000; Uehori, et al. *Infection and Immunity* 71: 4238-4249: 2003), lipoarabinomannan (Underhill, et al. *Proc Nat Acad Sci* 96:14459-14463: 1999; Means, at al. *J Immunol* 163:3920-3927: 1999; Tapping, at al. *Journal of Endotoxin Research* 9:264-268: 2003), a phenol-soluble modulin (Hajjar, at al, *J Immunol* 166:15-19: 2001), virions (Compton, at al. *Journal of Virology* 77:4588-4596: 2003), glycoinositolphospholipids (Campos, et al. *J Immunol* 167: 416-423: 2001), glycolipids (Opitz, et al. *The Journal of Biological Chemistry* 276:22041-22047: 2001), lipid A (Onier, et al. *International Journal of Cancer* 81:755-760: 1999; Onier, at al. *Clinical & Experimental Metastasis* 17:299-306: 1999), glycolipoprotein (Lopez, at al, *J Immunol* 170:2409-2416: 2003), lipoproteins/lipopeptides (Ozinsky, at al. *Proc Nat Acad Sci* 97:13766-13771: 2000; Hirschfeld, at al. *J Immunol* 163:2382-2386: 1999), zymosan (Underhill, at al. *Nature* 401:811-815: 1999), heat shock proteins (HSPs) (Ohashi, at al, *J Immunol* 164:558-561: 2000; Asea, et al. *The Journal of Biological chemistry* 277:15028-15034: 2002), extracellular matrix (ECM) components (biglycan or hyaluronan) (Schaefer, at al. *The Journal of Clinical investigation* 115:2223-2233: 2005; Jiang, at al. *Nature Medicine* 11:1173-1179: 2005), high-mobility group box 1 (HMGB1) (Park, et al. *The Journal of Biological Chemistry* 279:7370-7377: 2004), bacterial or viral proteins (Basu, et al. *The Journal of Biological Chemistry* 282:1039-1050: 2007), lipophosphoglycan (LPG) (Becker, et al. *Molecular and Biochemical Parasitology* 130:65-74: 2003), macrophage-activating lipopeptide-2 (MALP-2) (Takeuchi, et al. *International Immunology* 13:933-940: 2001; Schneider, et al. *Gut* 53:355-361: 2004), heat-killed bacterial or yeast (Flo, et al. *J Immunol* 164:2064-2069: 2000; Netea, et al. *J Immunol* 172:3712-3718: 2004; Taylor, et al. *The Journal of allergy and Clinical Immunology* 117:1148-1154: 2004), outer membrane protein A (Jeannin, et al *Nature Immunology* 1:502-509: 2000), soluble factors (Wyllie, et al. *J Immunol* 165:7125-7132: 2000; Henneke, et al. *J Immunol* 167:7069-7076: 2001), and lipoteichoic acid (LTA) (Schwandner, et al. *The Journal of Biological Chemistry* 274:17406-17409: 1999; Han, et al. *Infection and Immunity* 71:5541-5548: 2003; Schroder, et al, *The Journal of Biological Chemistry* 278:15587-15594: 2003). Studies also suggest that the variety of ligands recognized by TLR2 is due to the formation of heterodimer with other TLRs, TLR1 or TLR6 (Bauer, et al. *Proc Nat Acad Sci* 98:9237-9242: 2001; Sugawara, et al. *Microbiology and Immunology* 47:327-336: 2003; Takeuchi, et al. *Gene* 231: 59-65: 1999). The heterodimer of TLR1/TLR2 has been suggested to recognize triacylated lipoproteins, while TLR2/TLR6 recognizes diacylated lipoproteins (Takeuchi, et al. *J Immunol* 169:10-14: 2002).

While the method and agent have been described in terms of what are presently considered to be the most practical and preferred implementations, it is to be understood that the disclosure need not be limited to the disclosed exemplary implementations it is apparent that modifications and adaptations of those implementations will occur to those skilled in the art. It is intended to cover various modifications and similar arrangements included within the spirit and scope of the claims, the scope of which should be accorded the broadest interpretation so as to encompass all such modifications and similar structures. The present disclosure includes any and all implementations of the following claims.

What is claimed is:

1. A method for inhibiting growth of cancer cells in a subject in need thereof, comprising:
    administering to the subject a therapeutically effective amount of fibrillar albumin.

2. The method of claim 1, wherein the cancer cells are selected from the group consisting of kidney cancer cells, breast cancer cells, lung cancer cells, prostate cancer cells, liver cancer cells, and ovarian cancer cells.

3. The method of claim 1, wherein the fibrillar albumin causes an inhibition of the growth of the cancer cell in a dose-dependent manner.

4. The method of claim 1, further comprising causing the fibrillar albumin to bind to integrin α5β1 of the cancer cells.

5. The method of claim 1, wherein the fibrillar albumin inhibits the growth of the cancer cells via binding to integrin α5β1 of the cancer cells.

6. The method of claim 1, further comprising causing an increases in caspase-3 activity of the cancer cells.

7. The method of claim 1, further comprising causing apoptosis of the cancer cells.

8. A method of inhibiting proliferation and/or causing apoptosis of cancer cells in a subject in need thereof, comprising:
    administering to the subject a composition comprising a therapeutically effective amount of fibrillar albumin and a pharmaceutically acceptable carrier.

9. The method of claim 8, wherein the cancer cells are selected from the group consisting of kidney cancer cells, breast cancer cells, lung cancer cells, prostate cancer cells, liver cancer cells, and ovarian cancer cells.

10. The method of claim 8, wherein the fibrillar albumin inhibits the proliferation and/or causes apoptosis of the cancer cells in a dose-dependent manner.

11. The method of claim 8, further comprising causing the fibrillar albumin to bind to integrin α5β1 of the cancer cells.

12. The method of claim 8, wherein the fibrillar albumin increases caspase-3 activity of the cancer cells.

13. The method of claim 1, prior to the administering step further comprising:
    (a) preparing the fibrillar albumin from an isolated and/or purified globular albumin, comprising:
        (i) forming a solution containing the isolated and/or purified globular albumin;
        (ii) adding a detergent to the solution containing the isolated and/or purified globular albumin, wherein the detergent is one selected from the group consisting of sodium dodecyl sulfate (SDS) and n-tetradecyl-N,N-dimethyl-3-ammonio-1-propanesulfonate;
        (iii) applying the solution to a molecular sizing column with a pore size that permits separation of a protein with a molecular weight of at least about 70 kDa so as to promote column-induced formation of the fibrillar albumin from the isolated and/or purified globular albumin; and
        (iv) eluting the fibrillar albumin from the column, wherein the eluted albumin has a fibrillar structure.

14. The method of claim 13, wherein the detergent is added to the solution to a final concentration of 1%.

15. The method of claim 13, wherein the detergent comprises SDS.

16. The method of claim 13, wherein the step (a) further comprises preparing the composition comprising a therapeutically effective amount of the fibrillar albumin, and the pharmaceutically acceptable carrier.

17. The method of claim 13, wherein the cancer cells are selected from the group consisting of kidney cancer cells, breast cancer cells, lung cancer cells, prostate cancer cells, liver cancer cells, and ovarian cancer cells.

18. The method of claim 13, further comprising causing apoptosis of the cancer cells in the subject.

* * * * *